US012779014B2

(12) United States Patent
Pireaux et al.

(10) Patent No.: US 12,779,014 B2
(45) **Date of Patent: *Nov. 3, 2026**

(54) ANTICOAGULANT PROTEINS AND THEIR USE FOR TREATING DISEASES ASSOCIATED WITH THE ACTIVATION OF NEUTROPHILS

(71) Applicant: BIOXODES, Marche-en-Famenne (BE)

(72) Inventors: Valérie Pireaux, Namur (BE); Stéphanie Demoulin, Antheit (BE); Edmond Godfroid, Brussels (BE); Joël Tassignon, Roux (BE); Sandrine Derochette, Huccorgne (BE); Michel Guyaux, Woluwe-Saint-Pierre (BE)

(73) Assignee: BIOXODES, Marche-en-Famenne (BE)

( * ) Notice: Subject to any disclaimer, the term of this patent is extended or adjusted under 35 U.S.C. 154(b) by 0 days.

This patent is subject to a terminal disclaimer.

(21) Appl. No.: 19/230,637

(22) Filed: Jun. 6, 2025

(65) Prior Publication Data

US 2025/0295734 A1 Sep. 25, 2025

Related U.S. Application Data

(63) Continuation of application No. 18/394,080, filed on Dec. 22, 2023, which is a continuation-in-part of application No. 16/966,747, filed as application No. PCT/EP2019/052542 on Feb. 1, 2019, now abandoned.

(60) Provisional application No. 62/624,997, filed on Feb. 1, 2018.

(30) Foreign Application Priority Data

Jul. 27, 2018 (EP) .................................... 18186061

(51) Int. Cl.
*A61K 38/17* (2006.01)
*A61P 7/02* (2006.01)

(52) U.S. Cl.
CPC ............ *A61K 38/1767* (2013.01); *A61P 7/02* (2018.01)

(58) Field of Classification Search
None
See application file for complete search history.

(56) References Cited

U.S. PATENT DOCUMENTS 11,897,924 B2 * 2/2024 Demoulin .......... C07K 14/8114
2016/0046728 A1 2/2016 Godfroid et al.

FOREIGN PATENT DOCUMENTS

EP 1892297 A2 2/2008
EP 2123670 A1 * 11/2009 ......... C07K 14/8121

OTHER PUBLICATIONS

Attwood, T.K., Science. Oct. 20, 2000;290(5491):471-3. doi: 10.1126/science.290.5491.471. PMID: 11183771.*
Skolnick et al., Trends Biotechnol. Jan. 2000;18(1):34-9. doi: 10.1016/s0167-7799(99)01398-0. PMID: 10631780.*
Stryer, L., Biochemistry, 4th edition, W. H. Freeman and Company, 1995, pp. 18-23.*
Nieswandt et al., J Physiol. Sep. 1, 2011;589(17):4115-23. doi: 10.1113/jphysiol.2011.212886. Epub Jul. 18, 2011. PMID: 21768262 PMCID: PMC3180572.*
Schuhmann et al., J Neuroinflammation. Jan. 21, 2017;14(1):18. doi: 10.1186/s12974-017-0792-y. PMID: 28109273 PMCID: PMC5251224.*
Rudikoff et al., Proc Natl Acad Sci U S A. Mar. 1982;79(6):1979-83. doi: 10.1073/pnas.79.6.1979. PMID: 6804947 PMCID: PMC346105.*
Winkler et al., J Immunol. Oct. 15, 2000;165(8):4505-14. doi: 10.4049/jimmunol.165.8.4505. PMID: 11035090.*
Lin et al., J Gen Physiol. Oct. 2014;144(4):311-20. doi: 10.1085/jgp.201411247. Epub Sep. 15, 2014. PMID: 25225552 PMCID: PMC4178940.*
Jiao et al., J Biol Chem. May 8, 2020;295(19):6252-6262. doi: 10.1074/jbc.RA120.012605. Epub Mar. 26, 2020. PMID: 32217694 PMCID: PMC7212630.*
Gencic et al., J Neurosci. Jan. 1990;10(1):117-24. doi: 10.1523/JNEUROSCI.10-01-00117.1990. PMID: 1688931 PMCID: PMC6570349.*
Whisstock et al., Quarterly Reviews of Biophysics, 2003, 36:307-340.*
Braganza et al. New insights into atherosclerotic plaque rupture. Postgrad Med J 2001 ;77:94-98 (Year: 2001).
Choi et al. The Pathogenesis of Systemic Lupus Erythematosus—An Update. Curr Opin Immunol. Dec. 2012; 24(6): 651-657(Year: 2012).
Darbousset "lr-CPI: An original inhibitor of thrombosis and thrombosis-associated with cancer" Research and Practice in Thrombosis and Haemostasis, 2018: 2(1):244-245.
Darbousset, R., et al. (2012). "Tissue factor-positive neutrophils bind to injured endothelial wall and initiate thrombus formation." Blood. 120(10):2133-2143.
Darbousset, R., et al. (2014). "P2X1 expressed on polymorphonuclear neutrophils and platelets is required for thrombosis in mice." Blood. 124(16):2575-2585.
Database Geneseq "lxodes ricinus lr-CPI protein Seq ID No. 36" Database accession No. BCM20403.
Decrem, Y., et al. (2009). "lr-CPI, a coagulation contact phase inhibitor from the tick lxodes ricinus, inhibits thrombus formation without impairing hemostasis." J Exp Med. 206(11):2381-2395.

(Continued)

*Primary Examiner* — Michael Szperka
(74) *Attorney, Agent, or Firm* — NIXON & VANDERHYE

(57) ABSTRACT

Disclosed is an *Ixodes ricinus* salivary gland polypeptide and its use for inhibiting the extrinsic coagulation pathway and for treating and/or preventing diseases and conditions, such as thrombotic events, associated with the recruitment and activation of neutrophils following activation of the extrinsic coagulation pathway.

10 Claims, 15 Drawing Sheets

Specification includes a Sequence Listing.

(56) References Cited

OTHER PUBLICATIONS

Demers, M., et al. (2012). "Cancers predispose neutrophils to release extracellular DNA traps that contribute to cancer-associated thrombosis." Proc Natl Acad Sci U S A. 109(32):13076-13081.
Demouliri et al. Dual inhibition of factor XIIa and factor XIa as a therapeutic approach for safe thromboprotection. J Thromb Haemost.. Feb. 2021;19(2):323-329 (Year: 2021).
Dubois, C., et al. (2006). "Glycoprotein VI-dependent and -independent pathways of thrombus formation in vivo." Blood. 107(10):3902-3906.
Dubois, C., et al. (2007). "Thrombin-initiated platelet activation in vivo is vWF independent during thrombus formation in a laser injury model." J Clin Invest; 117(4):953-960.
Eliason et al. Neutrophil Depletion Inhibits Experimental Abdominal Aortic Aneurysm Formation. Circulation. 2005;112:232-240.) Year: 2005).
Falati, S., et al. (2002). "Real-time in vivo imaging of platelets, tissue factor and fibrin during arterial thrombus formation in the mouse." Nat Med. 8(10):1175-1181.
Futosi, K., et al. (2013). "Neutrophil cell surface receptors and their intracellular signal transduction pathways." Int Immunopharmacol. 17(3):638-650.
Goldmann et al. Neutrophil activation precedes myocardial injury in patients with acute myocardial infarction. Free Radical Biology & Medicine 47 (2009) 79-83 (Year: 2009).
Hu, Y. (2012). "Isolation of human and mouse neutrophils ex vivo and in vitro." Methods Mol Biol. 844:101-113.
International Search Report and Written Opinion of the ISA for PCT/EP2019/052542 dated Mar. 8, 2019, 12 pages.
Kambas, K., et al. (2012). "The emerging role of neutrophils in thrombosis-the journey of TF through NETs." Front Immunol. 3:385.
Kaplan et al. Pathways for bradykinin formation and inflammatory disease. J Allergy Olin ImmunolVolume 109, No. 2 (Year: 2002).
Kenny et al. A handshake between platelets and neutrophils might fuel deep vein thrombosis. Platelets, 3 1:5, 624-626, (Year: 2020).
Keularts, I. M., et al. (2001). "The role of factor XI in thrombin generation induced by low concentrations of tissue factor." Thromb Haemost. 85(6):1060-1065.
Leal, A. C., et al. (2017). "Tumor-Derived Exosomes Induce the Formation of Neutrophil Extracellular Traps: Implications For The Establishment of Cancer-Associated Thrombosis." Sci Rep. 7(1):6438.
Massberg, S., et al. (2010). "Reciprocal coupling of coagulation and innate immunity via neutrophil serine proteases." Nat Med. 16(8):887-896.
Mauracher, L. M., et al. (2018). "Citrullinated histone H3, a biomarker of neutrophil extracellular trap formation, predicts the risk of venous thromboembolism in cancer patients." J Thromb Haemost.
Mezouar, S., et al. (2015). "Inhibition of platelet activation prevents the P-selectin and integrin-dependent accumulation of cancer cell microparticles and reduces tumor growth and metastasis in vivo." Int J Cancer. 136(2):462-475.
Muller et al. Factor XI arid XII as antithrombotic targets. Current Opinion in Hematology 2011, 18:349-355 (Year: 2011).
Pengfei et al, "The extrinsic coagulation cascade and tissue factor pathway inhibitor in marcrophages: A potential therapeutic opportunity for artherosclerotic thrombosis" Thrombosis Research, 2014; 133(4):657-666.
Shen et al. Neutrophil dysregulation during sepsis: an overview and update. J. Cell. Mol. Med. vol. 21, No. 9, 2017 pp. 1687-1697 Year: 2017).
Stavrou et al. Factor XII and uPAR upregulate neutrophil functions to influence wound healing. (J. Clin. Invest. 2018; 128(3): 944-959) (Year: 2018).
Thomas, G. M., et al. (2009). "Cancer cell-derived microparticles bearing P-selectin glycoprotein ligand 1 accelerate thrombus formation in vivo." J Exp Med. 206(9):1913-1927.
Tuma et al. (Microcirculatiori by Tuma et al.—Google book p. 430) (Year: 2011).
Von Bruhl, M. L., et al. (2012). "Monocytes, neutrophils, and platelets cooperate to initiate and propagate venous thrombosis in mice in vivo." J Exp Med. 209(4):819-835.
Waleed et al, "Recombinant human tissue factor pathway inhibitor prevents thrombosis in a venous tuck model" The Laryngoscope, 2010; 120(11): 2172-2176.
Wu et al. Contact pathway of coagulation and inflammation. Thrombosis Journal (2015) 13:17 (Year: 2015).
Zheng et al. Donor pulmonary intravascular nonclassical monocytes recruit recipient neutrophils and mediate primary lung allograftdysfunction. Sci. Transl. Med. 2017. vol. 9, Issue 394 (Year: 2017).

* cited by examiner

ANTICOAGULANT PROTEINS AND THEIR USE FOR TREATING DISEASES ASSOCIATED WITH THE ACTIVATION OF NEUTROPHILS

CROSS-REFERENCE TO RELATED APPLICATIONS

This application is a continuation of U.S. application Ser. No. 18/394,080 filed Dec. 22, 2023, which is a continuation-in-part of U.S. application Ser. No. 16/966,747 filed Jul. 31, 2020, which is the U.S. national phase of International Application No. PCT/EP2019/052542 filed Feb. 1, 2019, which designated the U.S. and claims priority to provisional application No. 62/624,997 filed Feb. 1, 2018, and which also claims the benefit of EP application No. 18186061.0 filed Jul. 27, 2018, the entire contents of each of which are hereby incorporated by reference.

REFERENCE TO AN ELECTRONIC SEQUENCE LISTING

The contents of the electronic sequence listing (8453-0009_SEQ_ID.xml; Size: 4,708 bytes; and Date of Creation: Jun. 4, 2025) is herein incorporated by reference in its entirety.

FIELD OF INVENTION

The present invention relates to proteins and polypeptides comprising an *Ixodes ricinus* salivary gland polypeptide, and their use for treating and/or preventing diseases and conditions associated with the activation of neutrophils.

BACKGROUND OF INVENTION

Hemostasis is a vital function that stops bleeding and protects the integrity of blood circulation on both molecular and macroscopic levels. Hemostasis includes a coagulation cascade traditionally divided into two converting enzymatic cascades that are triggered either by blood-borne components of the vascular system (the intrinsic pathway) or by exposure of blood to a damaged vessel wall (the extrinsic pathway).

The intrinsic pathway and the contact phase (also referred to as the plasma kallikrein-kinin system), is initiated by contact phase proteins including the zymogens Factor XII (FXII), Factor XI (FXI) and prekallikrein (pKK or PK), as well as the cofactor high molecular weight kininogen (HK). Factor XII undergoes autoactivation when bound to negatively charged surfaces, generating activated Factor XII (FXIIa or αFXIIa) by a conformation change. αFXIIa then converts PK into activated plasma kallikrein (KK or PKa). Once small amounts of PKa are formed, they catalyze the conversion of surface-bound Factor XII into αFXIIa leading to strong positive feedback on the system. During this process, the activation of Factor XII leads to a succession of proteolysis steps leading to the production of a series of different active enzymes (XIa, IXa, VIIIa, Xa) which ultimately leads to activation of pro-thrombin in thrombin and formation of fibrin.

The extrinsic coagulation pathway, or Tissue Factor (TF) pathway, consists of a number of serine proteases, cofactors, calcium, and cell membrane components. The extrinsic coagulation pathway is activated by TF, also called platelet Tissue Factor, Factor III, thromboplastin, or CD142, which is expressed in the subendothelial layer. The extrinsic coagulation pathway is thus triggered by the binding of TF produced by exposed subendothelial cells to plasma Factor VII. The resulting complex initiates the coagulation cascade, converts Factor X into Factor Xa which ultimately leads to thrombin generation. Thrombin activates platelets and converts fibrinogen into fibrin. Both platelets and fibrin are essential elements of the hemostatic plug that is responsible for sealing the vascular breach. The extrinsic pathway is proposed to be the primary activator of the coagulation protease cascade in vivo. Subsequently, propagation of the thrombus involves recruitment of additional platelets and amplification of the coagulation cascade.

Moreover, under pathologic conditions such as inflammatory stimuli, TF is expressed by monocytes, neutrophils, endothelial cells, and platelets, which results in an elevation of the levels of circulating TF-positive microparticles. Therefore, the extrinsic coagulation pathway, besides activation of coagulation factors, also involves cells. Importantly, platelets play a critical role in the amplification of the coagulation cascade by providing a thrombogenic surface.

Studies conducted over the last decade support the growing notion that neutrophils contribute significantly to the thrombotic process. The attenuation of thrombotic manifestations in thrombotic animal models depleted for neutrophils demonstrates the contribution of these cells in thrombosis. Neutrophils can contribute to the pathologic venous and arterial thrombosis by the release of neutrophil extracellular traps (NETs). NET release is emerging as a major contributor to thrombogenesis in pathologic conditions such as sepsis, deep vein thrombosis and malignancy. In addition, it is suggested that NETs provide the scaffold for fibrin deposition and platelet entrapment and subsequent activation. Moreover, blood-cell derived microparticles, including those from neutrophils, have been involved in thrombus formation. Several studies also support the in vivo and ex vivo TF production by neutrophils (Kambas et al., 2012).

The active role of neutrophils in in vivo experimental thrombosis and inflammation-driven thrombotic diseases has been demonstrated. A contribution of neutrophils in the activation of the extrinsic coagulation cascade is the degradation of TFPI via elastase release, TFPI being the main inhibitor of TF (Massberg et al., 2010). In addition, it was demonstrated that neutrophil binding to the injured endothelium was the initial step in the continuum of events that results in thrombus formation in a model of laser-induced endothelial injury. The critical role of neutrophils was reinforced by the observation that these cells were the main source of TF, which was required for thrombus formation. It was shown that inhibition of neutrophil binding to the vessel wall reduces the presence of TF and diminishes the generation of fibrin and platelet accumulation (Darbousset et al., 2012; Darbousset et al., 2014). Moreover, in the same model, Factor XII deficiency did not attenuate thrombus generation (Darbousset et al., 2012). Thus, neutrophils play an important role in the activation of extrinsic coagulation system and NETs could provide the scaffold for fibrin deposition and platelet entrapment and subsequent activation.

For the past fifty years, anticoagulant treatment has been dominated by two classes of agents: heparins and antivitamins K. Heparins accelerate the inhibitory action of antithrombin on some activated coagulation factors (specifically thrombin and Factors IXa and Xa) by indirect inhibition of these factors and are only active when administered parenterally. Antivitamins K prevent the final synthesis of four coagulation factors (prothrombin and Factors VII, IX and X). Both classes of agents inhibit the extrinsic pathway of coagulation. However, the therapeutic window of these agents is narrow, requiring careful monitoring of patients. Indeed, these agents require careful laboratory testing in order to guarantee sufficient antithrombotic effectiveness while avoiding the risk of hemorrhage.

Thus, there is a strong need for new anticoagulants with no hemorrhagic side effects.

The Applicant previously demonstrated that polypeptides isolated from the salivary gland of the tick *I. ricinus*, Ir-CPI (*Ixodes ricinus* Contact Phase Inhibitor), specifically target coagulation Factors XIa and XIIa (EP1892297 and EP2123670; Decrem et al., 2009). *Ixodes ricinus* salivary gland polypeptides were thus found to be specific inhibitors of the intrinsic coagulation pathway. Indeed, in vitro, Ir-CPI was reported to prolong the activated Partial Thromboplastin Time (aPTT), showing interference with the intrinsic pathway, while having no effect on the Prothrombin Time (PT), the Thrombin Time (TT), and the dilute Russell's Viper Venom time (dRVVT), three tests triggering blood coagulation with activators of the extrinsic or common pathway. Moreover, in contrast to its strong dose-dependent reduction of thrombin generation induced by ellagic acid (intrinsic pathway activator), Ir-CPI was reported to be quite inactive in a thrombin generation assay in which thrombin generation was induced by low concentration of TF (5 pM) (extrinsic pathway activator). The small inhibition of thrombin generation with 5 pM of TF is explained by the fact that, at low concentrations of TF, thrombin can activate FXI of the intrinsic pathway in order to create a feedback-loop involving thrombin, FXI(a), FIX(a), FX(a) and (pro)thrombin, that sustains the extrinsic pathway (Keularts, Zivelin et al. 2001).

As a potential mechanism of action, the molecule was shown to inhibit activation of Factor XI and PK by Factor XIIa and of Factor XII by Factor XIa but was totally inactive on other targets of the coagulation pathways especially thrombin and Factor Xa which are the targets of the currently available parenteral and/or oral anticoagulant and antithrombotic drugs. Results previously disclosed were obtained in in vitro assays only involving factors of the coagulation pathways and, therefore, could not suggest an activity on cells involved in the extrinsic coagulation pathway.

Because of its specific effect on the intrinsic coagulation pathway, Ir-CPI is expected to have a larger therapeutic window regarding the risk of bleeding which constitutes the main side effect of current parenteral anticoagulants. As a matter of fact, the Applicant demonstrated that the molecule does not increase bleeding in an experimental model in rodents at pharmacological therapeutic active dose (Decrem, Rath et al., 2009).

The Applicant has now found that *Ixodes ricinus* salivary gland polypeptides unexpectedly inhibit the recruitment of polymorphonuclear neutrophils (PMNs) and platelets at the sites of lesion in an experimental mouse arteriolar laser injury model reported to be strictly dependent of TF and independent of FXII (Darbousset et al., 2012). In addition, the Applicant also found that, in vitro, *Ixodes ricinus* salivary gland polypeptides inhibit the activation of PMNs and the formation of neutrophil extracellular traps (also called NETosis). While not willing to be bound by any theory, the Applicant thus concludes that Ir-CPI inhibits the recruitment and activation of neutrophils at the site of lesion and thus plays a role in the recruitment and activation of neutrophils involved when the extrinsic coagulation pathway is activated.

Therefore, *Ixodes ricinus* salivary gland polypeptides are useful for the treatment and/or the prevention of diseases and conditions associated with the activation of the extrinsic coagulation pathway, such as, for example, thrombosis, and for the treatment and/or the prevention of inflammatory diseases with thrombotic tendency and thromboinflammation.

The discovery of these new features in the mechanism of action of Ir-CPI polypeptides makes of these molecule original compounds not only capable of inhibiting the intrinsic pathway but also capable to act on coagulation and/or thrombotic process involving TF but via a totally different mechanism that the inhibitors of thrombin and/or of Factors Xa.

The present invention thus relates to anticoagulant proteins comprising an *Ixodes ricinus* salivary gland polypeptide, and their use for treating and/or preventing diseases and conditions associated with the activation of neutrophils and/or NETosis.

SUMMARY

The present invention relates to a protein or polypeptide comprising a polypeptide that has at least 85% sequence identity with the amino acid sequence SEQ ID NO: 2 for use for inhibiting platelet recruitment, neutrophil recruitment, neutrophil activation and/or neutrophil extracellular trap formation (NETosis).

In one embodiment, inhibiting platelet recruitment, neutrophil recruitment, neutrophil activation and/or NETosis treats and/or prevents a disease or condition associated with platelet recruitment, neutrophil recruitment, neutrophil activation and/or NETosis.

In one embodiment, said disease or condition associated with platelet recruitment, neutrophil recruitment, neutrophil activation and/or NETosis is selected from the group comprising venous thrombosis, arterial thrombosis, thromboinflammation, and cardiovascular diseases. In one embodiment, said disease or condition associated with platelet recruitment, neutrophil recruitment, neutrophil activation and/or NETosis is thromboinflammation.

In one embodiment, said thromboinflammation is selected from the group comprising atherosclerosis, plaque rupture, devices-induced thromboinflammation, thrombosis induced by catheterism and/or stent positioning procedures, thrombosis induced by extracorporeal circulation, thrombus formation following cerebral injuries, coronary artery disease, acute myocardial infraction, cancer-associated thrombosis, metastasis-associated thrombosis, stroke-associated thrombosis, Behçet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis, inflammatory bowel diseases, heparin-induced thrombocytopenia, immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

In one embodiment, said thromboinflammation is thrombosis induced by catheterism and/or stent positioning procedures at the site of local vascular stenosis. In another embodiment, said thromboinflammation is blood-contacting medical devices-induced thromboinflammation. In another embodiment, said thromboinflammation is thrombosis and/or coagulation associated to the extracorporeal circulation.

The invention also relates to a pharmaceutical composition comprising a protein or polypeptide comprising a polypeptide that has at least 85% sequence identity with the amino acid sequence SEQ ID NO: 2 and at least one pharmaceutically acceptable excipient for use in inhibiting platelet recruitment, neutrophil recruitment, neutrophil activation and/or NETosis, and/or for treating and/or preventing a disease or condition associated with platelet recruitment, neutrophil recruitment, neutrophil activation and/or NETosis.

The invention also relates to a medicament comprising a protein or polypeptide comprising a polypeptide that has at least 85% sequence identity with the amino acid sequence SEQ ID NO: 2 for use in inhibiting platelet recruitment, neutrophil recruitment, neutrophil activation and/or NETosis, and/or for treating and/or preventing a disease or condition associated with platelet recruitment, neutrophil recruitment, neutrophil activation and/or NETosis.

Another object of the present invention is a medical device coated with an isolated polypeptide that has at least 85% sequence identity with the amino acid sequence SEQ ID NO: 2 for use in inhibiting platelet recruitment, neutrophil recruitment, neutrophil activation and/or NETosis, and/or for treating and/or preventing a disease or condition associated with platelet recruitment, neutrophil recruitment, neutrophil activation and/or NETosis.

Still another object of the present invention is a kit comprising a protein or polypeptide comprising an isolated polypeptide that has at least 85% sequence identity with the amino acid sequence SEQ ID NO: 2 for use in inhibiting platelet recruitment, neutrophil recruitment, neutrophil activation and/or NETosis, and/or for treating and/or preventing a disease or condition associated with platelet recruitment, neutrophil recruitment, neutrophil activation and/or NETosis.

The present invention further relates to a protein or polypeptide comprising a polypeptide that has at least 85% sequence identity with the amino acid sequence SEQ ID NO: 2 for use for inhibiting the extrinsic coagulation pathway in a subject in need thereof, wherein inhibiting the extrinsic coagulation pathway includes inhibiting platelet recruitment, neutrophil recruitment, neutrophil activation and/or neutrophil extracellular trap formation (NETosis).

The present invention also relates to a method for inhibiting the extrinsic coagulation pathway in a subject in need thereof, said method comprising administering to the subject a protein or polypeptide comprising an isolated polypeptide that has at least 85% sequence identity with the amino acid sequence SEQ ID NO: 2.

In one embodiment, said inhibition of the extrinsic coagulation pathway treats and/or prevents a disease or condition associated with the activation of the extrinsic coagulation pathway. In one embodiment, said inhibition of the extrinsic coagulation pathway treats and/or prevents thrombosis associated with the activation of the extrinsic coagulation pathway. In one embodiment, said inhibition of the extrinsic coagulation pathway treats and/or prevents venous thrombosis. In one embodiment, said inhibition of the extrinsic coagulation pathway treats and/or prevents arterial thrombosis. In one embodiment, said inhibition of the extrinsic coagulation pathway treats and/or prevents cancer-associated thrombosis. In one embodiment, said inhibition of the extrinsic coagulation pathway treats and/or prevents stroke-associated thrombosis. In one embodiment, said inhibition of the extrinsic pathway treats and/or prevents inflammatory diseases with thrombotic tendency. In one embodiment, said inhibition of the extrinsic pathway treats and/or prevents thromboinflammation.

The present invention also relates to a pharmaceutical composition comprising a protein or polypeptide comprising a polypeptide that has at least 85% sequence identity with the amino acid sequence SEQ ID NO: 2 and at least one pharmaceutically acceptable excipient for use for inhibiting the extrinsic coagulation pathway in a subject in need thereof as described hereinabove.

The present invention also relates to a medicament comprising a protein or polypeptide comprising a polypeptide that has at least 85% sequence identity with the amino acid sequence SEQ ID NO: 2 for use for inhibiting the extrinsic coagulation pathway in a subject in need thereof as described hereinabove.

The present invention also relates to a kit comprising a protein or polypeptide comprising a polypeptide that has at least 85% sequence identity with the amino acid sequence SEQ ID NO: 2 for use for inhibiting the extrinsic coagulation pathway in a subject in need thereof as described hereinabove.

The present invention also relates to a medical device coated with an isolated polypeptide that has at least 85% sequence identity with the amino acid sequence SEQ ID NO: 2 for use for inhibiting the extrinsic coagulation pathway in a subject in need thereof as described hereinabove.

Definitions

In the present invention, the following terms have the following meanings:

The term “about” preceding a value means plus or minus 10% of said value.

The term “amino acid substitution” refers to the replacement in a polypeptide of one amino acid with another amino acid. In one embodiment, an amino acid is replaced with another amino acid having similar structural and/or chemical properties, e.g., conservative amino acid replacements. “Conservative amino acid substitution” may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

The term “identity” refers to a measure of the identity of nucleotide sequences or amino acid sequences. In general, the sequences are aligned so that the highest order match is obtained. “Identity” per se has an art-recognized meaning and can be calculated using published techniques. See, e.g.: Computational Molecular Biology, Lesk, A. M., ed., Oxford University Press, New York, 1988; Biocomputing: Informatics And Genome Projects, Smith, D. W., ed., Academic Press, New York, 1993; Computer Analysis Of Sequence Data, Part I, Griffin, A. M., and Griffin, H. G., eds, Humana Press, New Jersey, 1994; Sequence Analysis In Molecular Biology, von Heijne, G., Academic Press, 1987; and Sequence Analysis Primer, Gribskov, M. and Devereux, J., eds, M Stockton Press, New York, 1991. While there exist a number of methods to measure identity between two polynucleotide or polypeptide sequences, the term "identity" is well known to skilled artisans (Carillo and Lipton, SIAM J Applied Math, 1998, 48:1073). Methods commonly employed to determine identity or similarity between two sequences include, but are not limited to, those disclosed in Guide to Huge Computers, Martin J. Bishop, ed., Academic Press, San Diego, 1994; and Carillo and Lipton, SIAM J Applied Math, 1998, 48:1073. Methods to determine identity and similarity are codified in computer programs. Preferred computer program methods to determine identity and similarity between two sequences include, but are not limited to, GCG program package (Devereux et al., J Molec Biol, 1990, 215:403). Most preferably, the program used to determine identity levels was the GAP program, as was used in the Examples below.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point-mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The term "peptide linker", also called "spacer peptide", refers to a peptide used to link 2 peptides or polypeptides together. In one embodiment, a peptide linker of the invention comprises from 3 to 50 amino acids. Peptide linkers are known in the art or are described herein.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. A pharmaceutically acceptable carrier or excipient refers to a non-toxic solid, semi-solid or liquid filler, diluent, encapsulating material or formulation auxiliary of any type. For human administration, preparations should meet sterility, pyrogenicity, general safety and purity standards as required by FDA Office of Biologics standards.

The term "polynucleotide" refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term Polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

The term "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

The term "protein" refers to a sequence of more than 100 amino acids and/or to a multimeric entity. The proteins of the invention are not limited to a specific length of the product. The term "polypeptide" or "protein" does not refer to or exclude post-expression modifications of the protein, for example, glycosylation, acetylation, phosphorylation and the like, as well as other modifications known in the art, both naturally occurring and non-naturally occurring. Such modifications are well described in basic texts and in more detailed monographs, as well as in a voluminous research literature. Modifications can occur anywhere in a polypeptide or protein, including the peptide backbone, the amino acid side-chains and the amino or carboxyl termini. It will be appreciated that the same type of modification may be present in the same or varying degrees at several sites in a given polypeptide or protein. Also, a given polypeptide or protein may contain many types of modifications. Polypeptides or proteins may be branched as a result of ubiquitination, and they may be cyclic, with or without branching. Cyclic, branched and branched cyclic polypeptides or proteins may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, "Proteins-structure and molecular properties", 2nd Ed., T. E. Creighton, W. H. Freeman and Comany, New York, 1993; Wolt, F., "Posttranslational Protein Modifications: Perspectives and Prospects", Posttranslational covalent modification of proteins, B. C. Johnson, Ed., Academic Press, New York, 1983, pgs. 1-12; Seifter et al., "Analysis for protein modifications and nonprotein cofactors", Meth Enzymol, 1990, 182:626-646; Rattan et al, "Protein Synthesis: Posttranslational Modifications and Aging", Ann NY Acad Sci, 1992, 663:48-62. A protein may be an entire protein, or a subsequence thereof.

An "isolated protein or polypeptide" is one that has been identified and separated and/or recovered from a component of its natural environment. In a preferred embodiment, the isolated protein or polypeptide will be purified (1) to greater than 80, 85, 90, 95% by weight of protein or polypeptide as determined by the Lowry method, and most preferably more than 96, 97, 98, or 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining.

Isolated protein or polypeptide includes the protein in situ within recombinant cells since at least one component of the protein's or polypeptide's natural environment will not be present. Ordinarily, however, isolated protein or polypeptide will be prepared by at least one purification step.

The term "fusion protein" refers to a molecule comprising two or more proteins or fragments thereof linked by a covalent bond via their individual peptide backbones, most preferably generated through genetic expression of a polynucleotide molecule encoding those proteins. The polypeptides forming the fusion protein are typically linked C-terminus to N-terminus, although they can also be linked C-terminus to C-terminus, N-terminus to N-terminus, or N-terminus to C-terminus. The polypeptides of the fusion proteins may be fused in any order.

The term "fused" refers to components that are linked by peptide bonds, either directly or through one or more peptide linkers.

The term "native Ir-CPI" refers to naturally occurring Ir-CPI, as opposed to a "modified Ir-CPI" or "optimized Ir-CPI", which has been modified from a naturally occurring Ir-CPI, e.g., to alter one or more of its properties such as stability. A modified Ir-CPI polypeptide may for example comprise modifications in the amino acid sequence, e.g., amino acid substitutions, deletions or insertions.

The term "subject" refers to a mammal, preferably a human. In one embodiment, the subject is a man. In another embodiment, the subject is a woman. In one embodiment, a subject may be a "patient", i.e., a warm-blooded animal, more preferably a human, who/which is awaiting the receipt of, or is receiving medical care or was/is/will be the object of a medical procedure, or is monitored for the development of the disease or condition. In one embodiment, the subject is an adult (for example a subject above the age of 18). In another embodiment, the subject is a child (for example a subject below the age of 18).

The term "therapeutically effective amount" means the level or amount of agent that is aimed at, without causing significant negative or adverse side effects to the target, (1) delaying or preventing disease or condition associated to the recruitment of neutrophils, the activation of neutrophils or to the activation of the extrinsic coagulation pathway; (2) slowing down or stopping the progression, aggravation, or deterioration of one or more symptoms of disease or condition associated to the recruitment of neutrophils, the activation of neutrophils or to the activation of the extrinsic coagulation pathway; (3) bringing about ameliorations of the symptoms of disease or condition associated to the recruitment of neutrophils, the activation of neutrophils or to the activation of the extrinsic coagulation pathway; (4) reducing the severity or incidence of disease or condition associated to the recruitment of neutrophils, the activation of neutrophils or to the activation of the extrinsic coagulation pathway; or (5) preventing disease or condition associated to the recruitment of neutrophils, the activation of neutrophils or to the activation of the extrinsic coagulation pathway. In one embodiment, a therapeutically effective amount is administered prior to the onset of disease or condition associated to the recruitment of neutrophils, the activation of neutrophils or to the activation of the extrinsic coagulation pathway, for a prophylactic or preventive action.

The term "treating" or "treatment" or "alleviation" refers to both therapeutic treatment and prophylactic or preventative measures; wherein the object is to prevent or slow down (lessen) the disease or condition associated to the recruitment of neutrophils, the activation of neutrophils or to the extrinsic coagulation pathway. Those in need of treatment include those already affected with the disease or condition associated to the recruitment of neutrophils, the activation of neutrophils or to the extrinsic coagulation pathway as well as those prone to have the disease or condition associated to the recruitment of neutrophils, the activation of neutrophils or to the extrinsic coagulation pathway or those in whom the disease or condition associated to the recruitment of neutrophils, the activation of neutrophils or to the extrinsic coagulation pathway is to be prevented. A subject or mammal is successfully "treated" for an infection if, after receiving a therapeutic amount of a protein or polypeptide according to the methods of the present invention, the patient shows observable and/or measurable reduction in or absence of one or more of the following: reduction in the number of pathogenic cells; reduction in the percent of total cells that are pathogenic; and/or relief to some extent, one or more of the symptoms associated with the disease or condition associated to the recruitment of neutrophils, the activation of neutrophils or to the extrinsic coagulation pathway; reduced morbidity and mortality, and improvement in quality of life issues. The above parameters for assessing successful treatment and improvement in the disease or condition associated to the recruitment of neutrophils, the activation of neutrophils or to the extrinsic coagulation pathway are readily measurable by routine procedures familiar to a physician.

The term "variant" refers to a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions identical. A variant and reference polypeptide may differ in amino acid sequence by one or more substitutions (preferably conservative), additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide.

DETAILED DESCRIPTION

The present invention thus relates to a protein or polypeptide comprising an *Ixodes ricinus* salivary gland polypeptide or a fragment or a variant thereof, and its use for inhibiting the extrinsic coagulation pathway and thereby for treating and/or preventing diseases and conditions associated to the extrinsic coagulation pathway, in particular treating and/or preventing thrombus associated to the activation of the extrinsic coagulation pathway.

In one embodiment, the invention relates to a protein or polypeptide comprising an *Ixodes ricinus* salivary gland polypeptide or a fragment or a variant thereof, and its use for inhibiting the cellular part of the extrinsic coagulation pathway. In one embodiment, the terms "cellular part of the extrinsic coagulation pathway" means the platelet recruitment, activation of neutrophils and/or recruitment of neutrophils and/or NETs formation. Therefore, in one embodiment, inhibiting the cellular part of the extrinsic coagulation pathway consists of inhibiting the platelet recruitment, activation of neutrophils and/or recruitment of neutrophils and/or NETs formation.

In one embodiment, inhibiting the extrinsic coagulation pathway includes inhibiting platelet recruitment, neutrophil recruitment, neutrophil activation and/or NETosis. Therefore, in one embodiment, the invention relates to the use of a protein or polypeptide comprising an *Ixodes ricinus* salivary gland polypeptide or a fragment or a variant thereof, and its use for inhibiting platelet recruitment, neutrophil recruitment, neutrophil activation and/or NETosis. The invention also relates to the protein or polypeptide according to the invention for treating and/or preventing diseases and conditions associated to the platelet recruitment, the activation of neutrophils, the recruitment of neutrophils and/or NETosis.

In one embodiment, inhibiting the extrinsic coagulation pathway, in particular inhibiting the cellular part of the extrinsic coagulation pathway, consists of inhibiting platelet recruitment, neutrophil recruitment, neutrophil activation and/or NETosis.

In one embodiment, the invention relates to the use of a protein or polypeptide comprising an *Ixodes ricinus* salivary gland polypeptide or a fragment or a variant thereof for inhibiting the extrinsic coagulation pathway, preferably the cellular part of the extrinsic coagulation pathway, or for inhibiting platelet recruitment, neutrophil recruitment, neutrophil activation and/or NETosis.

In one embodiment, inhibiting the extrinsic coagulation pathway, in particular inhibiting the cellular part of the extrinsic coagulation pathway, does not include inhibiting tissue factors specific of the extrinsic coagulation pathway, such as Tissue Factor. In one embodiment, inhibiting the extrinsic coagulation pathway, in particular inhibiting the cellular part of the extrinsic coagulation pathway, does not include inhibiting coagulation factors specific of the extrinsic coagulation pathway.

In one embodiment, the protein or polypeptide of the invention is an isolated protein or polypeptide.

In one embodiment, the *Ixodes ricinus* salivary gland polypeptide of the invention is Ir-CPI (*Ixodes ricinus* Contact Phase Inhibitor). As used herein, Ir-CPI may also be called IrCPI.

According to one embodiment, the Ir-CPI polypeptide of the invention has an amino sequence comprising or consisting in the sequence SEQ ID NO: 1. In one embodiment, the Ir-CPI polypeptide of the invention is encoded by the cDNA corresponding to the amino acid sequence SEQ ID NO: 1.

In one embodiment, the amino acid sequence of the Ir-CPI polypeptide of the invention is at least 85% identical to SEQ ID NO: 1, preferably at least 90%, 95%, 96%, 97%, 98%, 99% or 100% identical.

In one embodiment, fragments of the Ir-CPI polypeptide are also included in the present invention. As used herein, the term "fragment" means a polypeptide having an amino acid sequence that is the same as part, but not all, of the amino acid sequence of the aforementioned Ir-CPI polypeptide. As with the Ir-CPI polypeptide, fragments may be "free-standing" or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of the polypeptide. In this context "about" includes the particularly recited ranges larger or smaller by several, 5, 4, 3, 2 or 1 amino acid at either extreme or at both extremes.

Preferred fragments include, but are not limited to, truncation polypeptides having the amino acid sequence of the Ir-CPI polypeptide, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are the fragments characterized by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate Ir-CPI polypeptide activity, including those with a similar activity or an improved activity, or with a decreased undesirable activity.

In one embodiment, all of these polypeptide fragments retain parts of the biological activity of the Ir-CPI polypeptide.

In one embodiment, variants of the Ir-CPI polypeptide are also included in the present invention. Preferred variants are those that vary from the Ir-CPI polypeptide by conservative amino acid substitutions, i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, or 1-2 amino acids are substituted, deleted, or added in any combination. Most preferred variants are naturally occurring allelic variants of the Ir-CPI polypeptide present in *Ixodes ricinus* salivary glands.

In one embodiment, the Ir-CPI polypeptide of the invention has an amino sequence comprising a mutation (substitution) leading to the replacement of Asparagine in a position corresponding to position 54 in the amino acid sequence of SEQ ID NO: 1 by Glutamine to prevent N-glycosylation.

In one embodiment, the Ir-CPI polypeptide of the invention has an amino sequence comprising or consisting in the sequence of SEQ ID NO: 2.

In one embodiment, the amino acid sequence of the Ir-CPI polypeptide of the invention is at least 85% identical to SEQ ID NO: 2, preferably at least 90%, 95%, 96%, 97%, 98%, 99% or 100% identical.

In one embodiment, the Ir-CPI polypeptide of the invention can be prepared in any suitable manner. Example of peptides prepared according to a suitable manner include, without being limited to, isolated naturally occurring polypeptides, recombinantly produced polypeptides, synthetically produced polypeptides, or polypeptides produced by a combination of these methods. Means for preparing such polypeptides are well understood in the art.

In one embodiment, the protein of the invention is a fusion protein comprising Ir-CPI.

As used herein, the term "fusion protein" refers to a fusion of the Ir-CPI polypeptide as described hereinabove and at least one other polypeptide.

In one embodiment, the Ir-CPI polypeptide is linked to at least one other polypeptide in such a manner as to produce a single protein which retains the biological activity of Ir-CPI.

In one embodiment, the polypeptides of the fusion protein are linked C-terminus to N-terminus. In another embodiment, the components of the fusion protein are linked C-terminus to C-terminus. In another embodiment, the components of the fusion protein are linked N-terminus to N-terminus. In another embodiment, the components of the fusion protein are linked N-terminus to C-terminus.

In one embodiment, the polypeptides of the fusion protein may be fused in any order.

In one embodiment, the polypeptides are disposed in a single, contiguous polypeptide chain.

In one embodiment, the fusion protein of the invention further comprises at least one peptide linker. In one embodiment, the polypeptides of the fusion protein of the invention are linked to each other through one or more peptide linkers.

In one embodiment, the term "Ir-CPI-fusion proteins" or "fusion proteins" indiscriminately refers to fusion proteins without a linker sequence added or with a linker sequence added.

In one embodiment, the linker peptide provides a greater physical separation between the two moieties and thus maximizes the availability of the *Ixodes ricinus* salivary gland polypeptide. The linker peptide may consist of amino acids such that it is flexible or more rigid.

In one embodiment, the peptide linker of the invention comprises from 1 to 60 amino acids, preferably from 2 to 50 amino acids, more preferably from 4 to 40 amino acids. In one embodiment, the peptide linker of the invention comprises from 5 to 50 amino acids, from 10 to 50 amino acids, from 15 to 50 amino acids, or from 20 to 50 amino acids. In another embodiment, the peptide linker of the invention comprises from 6 to 20 amino acids, from 8 to 20 amino acids, or from 10 to 20 amino acids. In another embodiment, the peptide linker of the invention comprises from 2 to 10 amino acids, from 5 to 20 amino acids, from 10 to 30 amino acids, or from 15 to 40 amino acids.

In one embodiment, the peptide linker of the invention is not an in vivo cleavable linker. In one embodiment, the peptide linker of the invention is an in vivo cleavable linker.

Fusion proteins of the invention may be obtained, for example, by solid-state peptide synthesis (e.g., Merrifield solid phase synthesis) or recombinant production. For recombinant production one or more polynucleotide encoding the fusion protein (fragment), e.g., as described hereinabove, is isolated and inserted into one or more vectors for further cloning and/or expression in a host cell. Such polynucleotide may be readily isolated and sequenced using conventional procedures.

Methods which are well known to those skilled in the art can be used to construct expression vectors containing the coding sequence of a fusion protein (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the fusion protein (fragment) (i.e., the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g., on a single vector, or in separate polynucleotide constructs, e.g., on separate (different) vectors. Furthermore, any vector may contain a single coding region, or may comprise two or more coding regions, e.g., a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the fusion protein (fragment) of the invention, or variant or derivative thereof. Heterologous coding regions include without limitation specialized elements or motifs, such as a secretory signal peptide or a heterologous functional domain. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g., the immediate early promoter, in conjunction with intron-A), simian virus 40 (e.g., the early promoter), and retroviruses (such as, e.g., Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g., promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Fusion proteins prepared as described herein may be purified by art-known techniques such as high-performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the fusion protein binds. The purity of the fusion protein can be determined by any of a variety of well-known analytical methods including gel electrophoresis, high pressure liquid chromatography, and the like.

The invention also relates to a polynucleotide or nucleic acid encoding a protein or polypeptide comprising an Ir-CPI polypeptide, a fragment or variant thereof as described hereinabove, and its use for inhibiting the extrinsic coagulation pathway, preferably for inhibiting the cellular part of the extrinsic coagulation pathway, or for inhibiting the recruitment of platelet, the recruitment of neutrophils, the activation of neutrophils and/or the NETosis, and thereby for treating and/or preventing diseases and conditions associated to the extrinsic coagulation pathway or to the recruitment of platelet, the recruitment of neutrophils, the activation of neutrophils and/or the NETosis.

According to one embodiment, the polynucleotide or nucleic acid of the invention has a nucleotide sequence comprising or consisting in the sequence SEQ ID NO: 3 or in a sequence with at least 70%, 75%, 80%, 85%, 90%, 95%, 96%, 97%, 98%, 99% or 100% identity with SEQ ID NO: 3.

In one embodiment, the polynucleotide encoding the polypeptide of the invention has the nucleotide sequence as set forth in SEQ ID NO: 3.

In one embodiment, the polynucleotides encoding the fusion proteins of the invention may be expressed as a single polynucleotide that encodes the entire fusion protein or as multiple (e.g., two or more) polynucleotides that are co-expressed. Polypeptides encoded by polynucleotides that are co-expressed may associate through, e.g., disulfide bonds or other means, to form a functional fusion protein.

In one embodiment, the polynucleotide or nucleic acid is DNA. In another embodiment, the polynucleotide or nucleic acid is RNA, for example, in the form of messenger RNA (mRNA). RNA of the present invention may be single stranded or double stranded.

Another object of the present invention is a vector comprising one or more polynucleotides encoding a protein or polypeptide of the invention, and its use for inhibiting the extrinsic coagulation pathway, preferably for inhibiting the cellular part of the extrinsic coagulation pathway, or for inhibiting the recruitment of platelet, the recruitment of neutrophils, the activation of neutrophils and/or the NETosis, and thereby for treating and/or preventing diseases and conditions associated to the extrinsic coagulation pathway or to the recruitment of platelet, the recruitment of neutrophils, the activation of neutrophils and/or the NETosis. In a preferred embodiment, the vector of the invention is an expression vector.

The invention also relates to a composition comprising a protein or polypeptide, a polynucleotide or nucleic acid, or a vector as described hereinabove.

The present invention further relates to a pharmaceutical composition comprising a protein or polypeptide, a polynucleotide or nucleic acid, or a vector of the invention, and at least one pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the invention is a medicament comprising a protein or polypeptide, a polynucleotide or nucleic acid, a vector, a composition, or a pharmaceutical composition as described hereinabove.

In one embodiment, the pharmaceutical composition or the medicament of the invention comprises a therapeutically effective amount of the protein or polypeptide, the polynucleotide or nucleic acid, or of the vector as described hereinabove.

A further object of the present invention is a medical device coated by a protein or polypeptide as described hereinabove.

Furthermore, another object of the present invention is the use of a protein or polypeptide as described hereinabove for coating a medical device. Still another object of the present invention is a protein or polypeptide as described hereinabove for coating a medical device.

Accordingly, the present invention also relates to a medical device coated with a protein or polypeptide as described hereinabove.

Examples of medical devices that may be coated by the protein or polypeptide of the invention include, but are not limited to, coronary stent, artificial heart, artificial heart valve, central venous line, cardioplegia delivery system, dilators, tunneling devices, stent grafts cannulae, catheters, extracorporeal circulation systems including but not limited to extracorporeal membrane oxygenation systems, (auto)

transfusion systems, arterial filters, hemodialysis systems, plasmapheresis systems; medical device used for collection of blood outside the body; and/or accessories for any one of said devices including but not limited to tubing, cannulae, centrifugal pump, valve, port, and/or diverter, arterial stents for stenosis and aneurysm, and left ventricular assist devices.

The invention relates to the use of a protein or polypeptide, a polynucleotide or nucleic acid, a vector, a composition, a pharmaceutical composition, a medicament or a coated medical device of the invention for inhibiting the extrinsic coagulation pathway, preferably for inhibiting the cellular part of the extrinsic coagulation pathway, more preferably for treating thrombotic diseases associated with the extrinsic coagulation pathway.

As described hereinabove, in one embodiment, inhibiting the extrinsic coagulation pathway, in particular inhibiting the cellular part of the extrinsic coagulation pathway, includes inhibiting platelet recruitment, neutrophil recruitment, neutrophil activation and/or NETosis.

The Applicant has surprisingly found that an Ir-CPI polypeptide according to the invention inhibits platelet recruitment, neutrophil recruitment, neutrophil activation and NETosis, thereby inhibiting thrombosis associated with the extrinsic coagulation pathway.

Indeed, the Applicant has shown that an Ir-CPI polypeptide revealed to be surprisingly protective in an experimental animal model of laser injury of the cremaster muscle arterioles wherein the extrinsic coagulation pathway is known to be the key factor leading to the thrombotic event (Darbousset et al., 2012). In this model, Ir-CPI inhibits not only the production of fibrin but also the recruitment of platelets at the site of the lesion. The Ir-CPI polypeptide was also active when the laser injury was applied on tumor-bearing mice in a model that is mainly dependent on Tissue Factor expressed by cancer cell-derived microparticles (Thomas et al., 2009). Since neutrophils play a key role in the activation of the Tissue Factor dependent pathway in the laser-injury model (Darbousset et al., 2012), the presence and activation of neutrophils were next compared in presence or absence of Ir-CPI. The Applicant observed that in vivo, Ir-CPI significantly inhibited the quantity of neutrophils accumulating and the neutrophil elastase activity at the site of injury. The Applicant also showed that in vitro, Ir-CPI significantly inhibited the activation of neutrophils primed with TNFα (tumor necrosis factor alpha) or incubated with Adenosine Triphosphate (ATP), as observed through the detection of the CD11b, CD11b activated or Ly6G expression at the surface of neutrophils. Upon activation, neutrophils may produce “neutrophil extracellular traps” (NETs), which are structures of chromatin filaments coated with histones, proteases and granular and cytosolic proteins. Studies suggest that NETs contribute to thrombosis by promoting fibrin deposition and platelet aggregation. The Applicant observed that in vitro, Ir-CPI also significantly diminished the formation of NETs (i.e., NETosis) by neutrophils primed with TNFα and activated with PAF (platelet-activating factor). The contribution of neutrophils in the generation of thrombotic events has been demonstrated in various experimental paradigms. The implication of autophagy in NETs release and Tissue Factor delivery to NETs and the link between NETs and thrombosis suggests a critical role for neutrophils in the interaction between inflammatory and thrombotic pathways (Demers et al., 2012; Leal et al., 2017; Mauracher et al., 2018). The attenuation of thrombotic manifestations in thrombotic animal models by neutrophil depletion demonstrates the contribution of these cells in thrombosis (von Brühl et al., 2012). The expression of produced and/or acquired TF by neutrophils suggests an involvement of these neutrophils in the pathogenesis of thrombotic events that characterize several inflammatory disorders. Thus, Ir-CPI inhibits thrombus formation following activation of the extrinsic coagulation pathway not through the inhibition of coagulation factors specific of this pathway, such as Tissue Factor, but through the inhibition of platelet recruitment, neutrophil recruitment, neutrophil activation and/or NET formation.

The Applicant has thus surprisingly found that an Ir-CPI polypeptide can be used in therapeutic indications aimed at preventing and/or treating thrombotic events in diseases and conditions wherein thrombosis and/or coagulation depends on the platelet recruitment, neutrophil recruitment, neutrophil activation and/or NET formation. The Applicant also demonstrated that Ir-CPI can be used in therapeutic indications aimed at preventing and/or treating thrombotic events in diseases and conditions associated with the activation of the extrinsic coagulation pathway.

Importantly, the Applicant clearly demonstrates that Ir-CPI binds to activated factors (FXIIa, FXIa, kallikrein), and to plasmin, but not to their zymogen forms, FXII, FXI, prekallikrein (PK), or plasminogen (Decrem et al., The Journal of experimental medicine vol. 206, 11 (2009): 2381-95). Results from clotting assays show that, in a dose-dependent manner, (i) Ir-CPI prolongs activated Partial Thromboplastin Time (aPTT), (ii) in a lesser extend it also prolongs the clot fibrinolysis time, and (iii) it reduces venous thrombus formation. In addition, it was demonstrated that Ir-CPI also inhibits FXIIa and FXIa clotting activities in aPTT-based coagulation tests designed with FXII or FXI deficient plasmas.

Of note, Stavrou, et al. (The Journal of clinical investigation vol. 128, 3 (2018): 944-959), highlighted a new role for FXII on stimulating neutrophil migration (decreased in FXII-deficient mice), and upregulating neutrophil functions, including the release of NETs. This activity is mediated by the binding of FXII zymogen to uPAR, in a zinc-dependent manner. The factor XII protein, which carries this neutrophil stimulating function, is in its zymogen form (not FXIIa), and is directly produced by neutrophils themselves. This neutrophil FXII is distinct from hepatic synthesized FXII present in blood circulation.

Importantly, neutralizing only the hepatic FXII synthesis (but not neutrophil FXII synthesis) has no impact on the effect of FXII on neutrophils, which is preserved provided that intrinsic neutrophil FXII synthesis occurs normally. Using Plasmon resonance studies, Ir-CPI was demonstrated to be unable to bind directly to FXII zymogen, and it was also unable to bind to the zymogen forms of FXI, PK or Plasminogen, as clearly shown by the Applicant (Decrem et al., 2009, The Journal of experimental medicine vol. 206, 11 (2009)): 2381-95). Therefore, the binding profile of Ir-CPI does not comply with any effect within the neutrophil upregulation mechanisms described by Stavrou, et al. (The Journal of clinical investigation vol. 128, 3 (2018): 944-959).

Hence, studies with Ir-CPI provide evidence that this protease inhibitor binds to the activated proteases, but not to their zymogen form. This is of particular relevance for FXII, for which only the activated form, FXIIa, can interact with Ir-CPI, as demonstrated by the Applicant (Decrem et al., 2009, The Journal of experimental medicine vol. 206, 11 (2009)). Conversely, the role of FXII for upregulating neutrophil functions, and favoring NETosis, among other activities, was demonstrated to be only dependent on the zymogen form, which is unreactive with Ir-CPI. Stavrou, et al. (The Journal of clinical investigation vol. 128, 3 (2018): 944-959) demonstrated that this activity is totally independent of FXIIa, and that it is not affected by blood circulation FXII, but only by endogenously synthesized FXII in neutrophils. Therefore, the effect of Ir-CPI observed on neutrophils and NETosis acts by a mechanism different from that involving the binding of FXII zymogen to neutrophil uPARs, in presence of Zn++.

In some embodiments, the protein or polypeptide of the invention binds to activated factors comprising FXIIa, FXIa, and kallikrein.

As used herein, "activated factors" or "activated coagulation factors" consists of activated forms of coagulation factors. As used herein, "activated factors" strictly excludes the zymogen forms of factors. As used herein, "activated factors" strictly consists of FXIIa, FXIa, and kallikrein, and strictly excludes the zymogen forms of said factors, namely FXII, FXI, and prekallikrein (PK), respectively.

In some embodiments, the protein or polypeptide of the invention does not bind to zymogen forms of factors. In some embodiments, the protein or polypeptide of the invention does not bind to zymogen forms of factors comprising FXII, FXI, and prekallikrein.

In some embodiments, the protein or polypeptide of the invention binds to activated coagulation factors comprising FXIIa, FXIa, and kallikrein. In some embodiments, the protein or polypeptide of the invention binds to activated factors (FXIIa, FXIa, kallikrein), and to plasmin, but not to their zymogen forms, FXII, FXI, prekallikrein (PK), or plasminogen. In some embodiments, the protein or polypeptide of the invention binds to activated factors comprising FXIIa, FXIa, and kallikrein, but not to the zymogen forms of the factors comprising FXII, FXI, and prekallikrein (PK), respectively. In some embodiments, the protein or polypeptide of the invention binds to activated factor FXIIa, but not its zymogen form FXII. In some embodiments, the protein or polypeptide of the invention binds to activated factor FXIa, but not its zymogen form FXI. In some embodiments, the protein or polypeptide of the invention binds to kallikrein, but not its zymogen form prekallikrein. In some embodiments, the protein or polypeptide of the invention binds to plasmin, but not its zymogen form plasminogen.

The invention relates to the use of a protein or polypeptide, a polynucleotide or nucleic acid, a vector, a composition, a pharmaceutical composition, a medicament or a coated medical device of the invention for treating and/or preventing diseases and conditions associated with the recruitment of platelet, activation of neutrophils, recruitment of neutrophils and/or NET formation in a subject in need thereof.

In one embodiment, treating and/or preventing diseases and conditions associated with the recruitment of platelets, activation of neutrophils, recruitment of neutrophils and/or NET formation in a subject in need thereof consists of treating and/or preventing diseases and conditions associated with the activation of the extrinsic coagulation pathway.

The invention relates to the use of a protein or polypeptide, a polynucleotide or nucleic acid, a vector, a composition, a pharmaceutical composition, a medicament or a coated medical device of the invention for treating and/or preventing diseases and conditions associated with the activation of the extrinsic coagulation pathway in a subject in need thereof, preferably thrombosis associated with the extrinsic coagulation pathway.

In one embodiment, the diseases and conditions associated with the activation of the extrinsic coagulation pathway are selected from the group comprising or consisting of thrombosis (including venous and arterial thrombosis), inflammatory diseases with thrombotic tendency, thromboinflammation (including devices-induced thromboinflammation), diseases and conditions associated to cardiac surgical interventions, cardiovascular diseases, cancer and metastasis.

Diseases and conditions associated with the activation of the extrinsic coagulation pathway include the inflammatory diseases with thrombotic tendency. As used herein, the term "inflammatory diseases with thrombotic tendency" may be replaced by "thrombotic complications in inflammatory diseases".

In one embodiment, the invention relates to the use of a protein or polypeptide, a polynucleotide or nucleic acid, a vector, a composition, a pharmaceutical composition, a medicament or a coated medical device of the invention for treating and/or preventing thrombosis associated with the activation of the extrinsic coagulation pathway in a subject in need thereof.

In one embodiment, thrombosis associated with the activation of the extrinsic coagulation pathway is selected from the group comprising or consisting of venous thrombosis, cancer-associated thrombosis and stroke-associated thrombosis. In one embodiment, the invention relates to the use of a protein or polypeptide, a polynucleotide or nucleic acid, a vector, a composition, a pharmaceutical composition, a medicament or a coated medical device of the invention for treating and/or preventing venous thrombosis. In another embodiment, the invention relates to the use of a protein or polypeptide, a polynucleotide or nucleic acid, a vector, a composition, a pharmaceutical composition, a medicament or a coated medical device of the invention for treating and/or preventing cancer-associated thrombosis. In another embodiment, the invention relates to the use of a protein or polypeptide, a polynucleotide or nucleic acid, a vector, a composition, a pharmaceutical composition, a medicament or a coated medical device of the invention for treating and/or preventing stroke-associated thrombosis.

Thus, in one embodiment, the invention relates to the use of a protein, a polynucleotide or nucleic acid, a vector, a composition, a pharmaceutical composition, a medicament or a coated medical device of the invention for treating and/or preventing inflammatory diseases with thrombotic tendency in a subject in need thereof.

In one embodiment, the invention relates to the use of a protein, a polynucleotide or nucleic acid, a vector, a composition, a pharmaceutical composition, a medicament or a coated medical device of the invention for treating and/or preventing thrombosis associated with inflammatory disease or thromboinflammation in a subject in need thereof.

As used herein, the term "thromboinflammation" refers to the uncontrolled development of blood clots with inflammation, and worsened by an excessive immune response.

Thromboinflammation is a common complication observed in broad range of human disorders or pathological conditions, playing a significant role in their progression and clinical outcomes. This phenomenon occurs most commonly in deep vein thrombosis, stroke, atherosclerosis, systemic inflammatory responses (e.g., sepsis), viral infection (e.g., COVID-19, malaria), bacterial infection (e.g., Gram+ bacteria), autoimmune disorders, cancer or chronic inflammatory diseases such as systemic lupus erythematosus or inflammatory bowel diseases. Several key components contribute to the development and perpetuation of thromboinflammation, such as platelets, endothelial cells, components of the hemostatic system, immune cells, inflammatory mediators, and reactive oxygen species (ROS). The immune reaction associated to thromboinflammation can occur in response to an injury, triggering an inflammatory response that involves immune cells such as neutrophils and monocytes, and various inflammatory mediators. Many therapeutics have been developed and tested to limit neutrophil-platelet interactions, considering their significant role in the pathogenesis of severe thromboinflammatory conditions.

In one embodiment, the invention relates to the use of a protein, a polynucleotide or nucleic acid, a vector, a composition, a pharmaceutical composition, a medicament or a coated medical device of the invention for treating and/or preventing an inflammatory disease with thrombotic tendency or a thromboinflammation selected from the group comprising or consisting of cancer-associated thrombosis, metastasis-associated thrombosis, stroke-associated thrombosis, Behçet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis, inflammatory bowel diseases, atherosclerosis and plaque rupture, coronary artery disease, acute myocardial infraction, thrombus formation following cerebral injuries, blood-contacting medical devices-induced thromboinflammation, thrombosis induced by catheterism and/or stent positioning procedures at the site of local vascular stenosis, thrombosis induced by extracorporeal circulation, heparin-induced thrombocytopenia (HIT), immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

In one embodiment, said thromboinflammation is selected from the group comprising or consisting of thrombosis induced by catheterism and/or stent positioning procedures at the site of local vascular stenosis, atherosclerosis, plaque rupture, coronary artery disease, devices-induced thromboinflammation. In one embodiment, devices-induced thromboinflammation includes blood-contacting medical devices-induced thromboinflammation. In another embodiment, said thromboinflammation is selected from the group comprising or consisting of cancer-associated thrombosis, metastasis-associated thrombosis, and stroke-associated thrombosis.

Diseases and conditions associated with the activation of the extrinsic coagulation pathway include blood contacting medical devices-induced thromboinflammation. In one embodiment, blood contacting medical devices-induced thromboinflammations include, but are not limited to, inflammations induced by catheterism (such as, for example, percutaneous transluminal angioplasty) and/or stent positioning procedures at the site of local vascular stenosis, considering the risk of atherosclerotic plaque rupture and subsequent risk of re-thrombosis and catheter thrombosis after such interventions; and extracorporeal circulation.

In one embodiment, the invention relates to the use of a protein or polypeptide, a polynucleotide or nucleic acid, a vector, a composition, a pharmaceutical composition, a medicament or a coated medical device of the invention for treating and/or preventing devices-induced thromboinflammation in a subject in need thereof.

Thus, in one embodiment, the invention relates to the use of a protein or polypeptide, a polynucleotide or nucleic acid, a vector, a composition, a pharmaceutical composition, a medicament or a coated medical device of the invention for treating and/or preventing thrombosis induced by catheterism (such as, for example, percutaneous transluminal angioplasty) and/or stent positioning procedures at the site of local vascular stenosis; and/or extracorporeal circulation in a subject in need thereof.

Diseases and conditions associated to the activation of the extrinsic coagulation pathway include thrombosis and/or coagulation associated to the extracorporeal circulation done within the context of a cardiac surgical intervention (e.g., coronary artery bypass graft surgery (CABG), open heart surgery).

Thus, in one embodiment, the invention relates to the use of a protein, a polynucleotide or nucleic acid, a vector, a composition, a pharmaceutical composition, a medicament or a coated medical device of the invention for treating and/or preventing thrombosis and/or coagulation associated to the extracorporeal circulation done within the context of a cardiac surgical intervention in a subject in need thereof.

Diseases and conditions associated with the activation of the extrinsic coagulation pathway include cancer, and in particular, cancer-associated thrombosis.

Indeed, microparticles containing Tissue Factor and NETosis have also been involved in thrombogenesis associated to cancer (Thomas et al., 2009; Demers et al., 2012; Mauracher et al., 2018).

Thus, in one embodiment, the invention relates to the use of a protein or polypeptide, a polynucleotide or nucleic acid, a vector, a composition, a pharmaceutical composition, a medicament or a coated medical device of the invention for treating and/or preventing cancer and/or metastasis in a subject in need thereof.

In one embodiment, cancers and/or metastasis are associated with the extrinsic coagulation pathway. In one embodiment, cancers and/or metastasis are associated with thrombosis. In a particular embodiment, the cancers and/or metastasis are associated with thrombosis associated with the extrinsic coagulation pathway.

In one embodiment, the invention relates to the use of a protein or polypeptide, a polynucleotide or nucleic acid, a vector, a composition, a pharmaceutical composition, a medicament or a coated medical device of the invention for treating and/or preventing cancer- and/or metastasis-associated thrombosis in a subject in need thereof.

In one embodiment, the invention relates to the use of a protein or polypeptide, a polynucleotide or nucleic acid, a vector, a composition, a pharmaceutical composition, a medicament or a coated medical device of the invention for treating and/or preventing stroke-associated thrombosis in a subject in need thereof.

The present invention also relates to a method of inhibiting platelet recruitment, neutrophil recruitment, neutrophil activation and/or NETosis in a subject in need thereof, comprising administering to said subject a therapeutically effective amount of a protein or polypeptide, polynucleotide or nucleic acid, vector, pharmaceutical composition, or medicament or coated medical device of the invention.

The present invention further relates to a method of treating and/or preventing a disease or condition associated with platelet recruitment, neutrophil recruitment, neutrophil activation and/or NETosis in a subject in need thereof, comprising administering to said subject a therapeutically effective amount of a protein or polypeptide, polynucleotide or nucleic acid, vector, pharmaceutical composition, or medicament or coated medical device of the invention.

In one embodiment, the method of the invention is for treating and/or preventing the diseases and conditions associated with the activation of the extrinsic coagulation pathway selected from the group comprising or consisting of venous thrombosis, arterial thrombosis, thromboinflammation, cardiovascular diseases, cancer and metastasis. The present invention also relates to a method of inhibiting the extrinsic coagulation pathway, preferably the cellular part of the extrinsic pathway, or for inhibiting the recruitment of platelet, the recruitment of neutrophils, the activation of neutrophils and/or the NETosis, in a subject in need thereof, comprising administering to said subject a therapeutically effective amount of a protein or polypeptide, polynucleotide or nucleic acid, vector, pharmaceutical composition, or medicament or coated medical device of the invention.

The present invention further relates to a method of treating and/or preventing a disease or condition associated with the recruitment of platelet, the recruitment of neutrophils, the activation of neutrophils and/or the NETosis in a subject in need thereof, comprising administering to said subject a therapeutically effective amount of a protein or polypeptide, polynucleotide or nucleic acid, vector, pharmaceutical composition, or medicament or coated medical device of the invention.

The present invention further relates to a method of treating and/or preventing a disease or condition associated with the extrinsic coagulation pathway in a subject in need thereof, comprising administering to said subject a therapeutically effective amount of a protein or polypeptide, polynucleotide or nucleic acid, vector, pharmaceutical composition, or medicament or coated medical device of the invention.

In one embodiment, the method of the invention is for treating and/or preventing the diseases and conditions associated with the activation of the extrinsic coagulation pathway, or with the recruitment of platelet, the recruitment of neutrophils, the activation of neutrophils and/or the NETosis, selected from the group comprising or consisting of thrombosis, inflammatory diseases with thrombotic tendency, devices-induced thromboinflammation, diseases and conditions associated to cardiac surgical interventions, and cancer and metastasis.

Another object of the invention is a method of treating and/or preventing inflammatory diseases with thrombotic tendency or thromboinflammation, in particular inflammatory disease associated thrombosis or thrombosis associated to an inflammatory disease, in a subject in need thereof, comprising administering to said subject a therapeutically effective amount of a protein or polypeptide, polynucleotide or nucleic acid, vector, pharmaceutical composition, or medicament or coated medical device of the invention.

In one embodiment, the method of the invention is for treating and/or preventing a disease or condition selected from the group comprising or consisting of inflammatory disease associated thrombosis, thrombosis associated to an inflammatory disease, cancer-associated thrombosis, metastasis-associated thrombosis, stroke-associated thrombosis, Behçet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis, inflammatory bowel diseases, atherosclerosis and plaque rupture, coronary artery disease, acute myocardial infraction, thrombus formation following cerebral injuries, blood-contacting medical devices-induced thromboinflammation, thrombosis induced by catheterism and/or stent positioning procedures at the site of local vascular stenosis, thrombosis induced by extracorporeal circulation, heparin-induced thrombocytopenia (HIT), immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

Another object of the invention is a method of treating and/or preventing thrombosis in all catheterism (such as, for example, percutaneous transluminal angioplasty) and/or stent positioning procedures at the site of local vascular stenosis in a subject in need thereof, comprising administering to said subject a therapeutically effective amount of a protein or polypeptide, polynucleotide or nucleic acid, vector, pharmaceutical composition, or medicament or coated medical device of the invention.

Another object of the invention is a method of treating and/or preventing thrombosis and/or coagulation associated to the extracorporeal circulation done within the context of a cardiac surgical intervention in a subject in need thereof, comprising administering to said subject a therapeutically effective amount of a protein or polypeptide, polynucleotide or nucleic acid, vector, pharmaceutical composition, or medicament or coated medical device of the invention.

Another object of the invention is a method of treating and/or cancer and/or metastasis, in particular cancer-associated thrombosis, in a subject in need thereof, comprising administering to said subject a therapeutically effective amount of a protein or polypeptide, polynucleotide or nucleic acid, vector, pharmaceutical composition, or medicament or coated medical device of the invention.

In one embodiment, the subject is susceptible to form thrombus, in particular thrombus associated with the extrinsic coagulation pathway. In one embodiment, the subject is at risk of developing thrombus, in particular thrombus associated with the extrinsic coagulation pathway. In another embodiment, the subject suffers or have suffered from thrombus, in particular thrombus associated with the extrinsic coagulation pathway.

Examples of risks of developing thrombus, in particular thrombus associated with the extrinsic coagulation pathway, include, but are not limited to the presence of an inflammatory diseases with thrombotic tendency, the presence of atherosclerotic lesions requiring an intervention aimed at facilitating local blood flow at the level of a vascular stenosis, the implementation of extracorporeal circulation, the Coronary Artery Bypass Grafting (CABG) associated with a Cardiopulmonary bypass, and the presence of cancer.

Extracorporeal circulation may in fact mediate thrombin generation by activation of the extrinsic pathway through the exposure of blood to air and TF in the wound and then the recirculation of this blood via cardiotomy suction used to reduce blood loss.

In one embodiment, the subject is susceptible to develop cancer and/or metastasis. In one embodiment, the subject is at risk of developing cancer and/or metastasis. In one embodiment, the subject suffers or have suffered from a cancer and/or metastasis.

In one embodiment, the subject recently underwent a surgery. By "recently", it is meant in one embodiment within 1 day, 2 days, 3 days, 4 days, 5 days, 6 days or more. In another embodiment, the term "recently" means within 2 hours, 4 hours, 6 hours, 12 hours, 18 hours or 24 hours.

In another embodiment, the subject is planned undergo a surgery. By "is planned to", it is meant in one embodiment within 2 hours, 4 hours, 6 hours, 12 hours, 18 hours or 24 hours. In another embodiment, the term "is planned to" means within 1 day, 2 days, 3 days, 4 days, 5 days, 6 days or more.

In one embodiment, the subject was not previously treated for thrombus. In another embodiment, the subject previously received one, two or more other treatments for thrombus.

As used herein, the term "treatment" encompasses prophylactic and therapeutic treatments.

In one embodiment, the subject of the invention is elderly. As used herein, the term "elderly" means that the subject is at least 50 years old, at least 55, 60, 65, 70, 75, 80, 85 or 90 years old.

In one embodiment, the subject is a man. In another embodiment, the subject is a woman.

It will be understood that the total daily usage of the protein of the invention, polynucleotide, vector, composition, pharmaceutical composition, medicament will be decided by the attending physician within the scope of sound medical judgment. The specific therapeutically effective dose level for any particular patient will depend upon a variety of factors including the disorder being treated and the severity of the disorder; activity of the specific agent employed; the specific composition employed, the age, body weight, general health, sex and diet of the patient; the time of administration, route of administration, and rate of excretion of the specific agent employed; the duration of the treatment; drugs used in combination or coincidental with the specific agent employed; and like factors well known in the medical arts. For example, it is well within the skill of the art to start doses of the agent at levels lower than those required to achieve the desired therapeutic effect and to gradually increase the dosage until the desired effect is achieved. However, the daily dosage of the products may be varied over a wide range from about 10 to about 10000 mg per adult per day, preferably 100 to about 5000, more preferably from about 200 to about 2000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10000 mg of the active ingredient, preferably 5 to about 5000, more preferably from about 10 to about 2000 mg of the active ingredient. An effective amount of the drug is ordinarily supplied at a dosage level from 0.01 mg/kg to about 100 mg/kg of body weight per day, preferably from about 0.05 mg/kg to 40 mg/kg of body weight per day, more preferably from about 0.1 mg/kg to 20 mg/kg of body weight per day, more preferably from about 0.2 mg/kg to 1 mg/kg of body weight per day.

For use in administration to a subject, the composition, pharmaceutical composition, medicament of the invention will be formulated for administration to the subject. The composition, pharmaceutical composition, medicament of the present invention may be administered orally, parenterally, topically, by inhalation spray, rectally, nasally, buccally, vaginally or via an implanted reservoir. The term administration used herein includes subcutaneous, intravenous, intramuscular, intraocular, intra-articular, intra-synovial, intrasternal, intrathecal, intrahepatic, intralesional and intracranial injection or infusion techniques.

In one embodiment, the composition, pharmaceutical composition, medicament of the invention is in a form adapted for topical administration.

Examples of forms adapted for topical administration include, but are not limited to, liquid, paste or solid compositions, and more particularly in form of aqueous solutions, drops, eye drops, ophthalmic solutions, dispersions, sprays, microcapsules, micro- or nanoparticles, polymeric patch, or controlled-release patch.

In one embodiment, the composition, pharmaceutical composition, or medicament of the invention comprises one or more pharmaceutical acceptable carrier for a formulation adapted for topical administration.

In one embodiment, the composition, pharmaceutical composition, or medicament of the invention is in a form adapted for injection, such as, for example, for intraocular, intramuscular, subcutaneous, intradermal, transdermal or intravenous injection or infusion.

Examples of forms adapted for injection include, but are not limited to, solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

Sterile injectable forms of the composition, pharmaceutical composition, medicament of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In a particular embodiment, the composition, pharmaceutical composition, or medicament of the invention is in a form adapted for intraocular administration.

In one embodiment, the composition, pharmaceutical composition, or medicament of the invention is administered to the subject in need thereof at least once a day. For example, the composition, pharmaceutical composition, or medicament of the invention may be administered once a day, twice a day, or three times a day. In a preferred embodiment, the composition, pharmaceutical composition, or medicament of the invention is administered to the subject in need thereof once a day.

In another embodiment, the composition, pharmaceutical composition, or medicament of the invention is administered to the subject in need thereof at least once a week. For example, the composition, pharmaceutical composition, or medicament of the invention may be administered once a week, twice a week, three times a week, four times a week or up to seven times a week.

In another embodiment, the composition, pharmaceutical composition, or medicament of the invention is administered to the subject in need thereof once a month, two times a month, every two months, every two or three months, two times a year or once a year.

In one embodiment, the composition, pharmaceutical composition, or medicament of the invention is administered to the subject in need thereof before being exposed to a risk to develop thrombus. In one embodiment, the term "before" means at least a week before the exposure. In another embodiment, the term "before" means five days, four days, three days, two days or one day before the exposure. In another embodiment, the term "before" means 24 hours, 18 hours, 15 hours, 12 hours, 6 hours, 4 hours, 2 hours or 1 hour before the exposure. In another embodiment, the term "before" means less than one hour before the exposure, such as 45 minutes, 30 minutes, 15 minutes, 10 minutes, 5 minutes before the exposure or at the moment of the exposure. As an illustration, the composition, pharmaceutical composition, or medicament of the invention may be administered to the subject 24 hours, 12 hours, 6 hours or 1 hour before a prolonged travel, or at the beginning of the prolonged travel.

In another embodiment, the composition, pharmaceutical composition, or medicament of the invention is administered to the subject in need thereof after being exposed to a risk to develop thrombus. In one embodiment, the term "after" means 5 minutes, 10 minutes, 15 minutes, 30 minutes, or 45 minutes after the exposure. In another embodiment, the term "after" means 1 hour, 2, 4, 6, 12, 15, 18 or 14 hours after the exposure. In another embodiment, the term "after" means 1 day, 2, 3, 4 or five days after the exposure. In another embodiment, the term "after" means a week or more after the exposure. As an illustration, the composition, pharmaceutical composition, or medicament of the invention may be administered to the subject immediately after a prolonged travel, 1 hour, 2 hours, 6 hours, or 12 hours after the prolonged travel.

In one embodiment, the coated medical device coated with the protein of the invention is formulated for administration to the subject. The coated medical device coated with the protein of the present invention may be administered parenterally or topically, or may implanted.

In one embodiment, the coated medical device coated with the protein of the invention is implanted in the cardiac or circulatory system.

The present invention also relates to a kit comprising a protein or polypeptide, polynucleotide or nucleic acid, vector, composition, pharmaceutical composition, or medicament or coated medical device according to the invention.

In one embodiment, the kit of the invention further comprises means to administer the protein or polypeptide, polynucleotide or nucleic acid, vector, composition, pharmaceutical composition, medicament or coated medical device to a subject in need thereof.

In one embodiment, the kit of the invention further comprises instructions for the administration of the protein or polypeptide, polynucleotide or nucleic acid, vector, composition, pharmaceutical composition, medicament or coated medical device to said subject.

In one embodiment, the kit of the invention is used for inhibiting the extrinsic coagulation pathway, in particular the cellular part of the extrinsic coagulation pathway, or for inhibiting the recruitment of platelet, the recruitment of neutrophils, the activation of neutrophils and/or the NETosis. In one embodiment, the kit of the invention is used for treating and/or preventing diseases and conditions associated to the activation of the extrinsic coagulation pathway. In one embodiment, the kit of the invention is used for treating and/or preventing thrombosis associated with the extrinsic coagulation pathway, preferably cancer-associated thrombosis. In one embodiment, the kit of the invention is used for preventing formation and/or thrombus growth of thrombosis associated with the extrinsic coagulation pathway. In one embodiment, the kit of the invention is used for treating and/or preventing cancer and/or metastasis.

BRIEF DESCRIPTION OF THE DRAWINGS

(FIG. 18A) Alphafold model of the catalytic domain of FXIIa (top) in complex with Ir-CPI (bottom). The complex is stabilized by an ionic interaction between R22 (S-1 site in Ir-CPI) and D538 and interactions between R24 (S+1 site in Ir-CPI) and the side chains of Y496, R413 as well as the with the backbone carbonyl of W486. An additional interaction between Q541 and the backbone carbonyl of C21 (Ir-CPI) further stabilizes the complex. (FIG. 18B) A similar binding mode between FXII (top) and Ir-CPI (bottom) shows that all the interactions described in panel A are absent. In particular, the position of R413 (stabilized by the FXII-specific conformation of D543) is incompatible with the position of R24, likely preventing formation of the complex.

EXAMPLES

Figure 1:
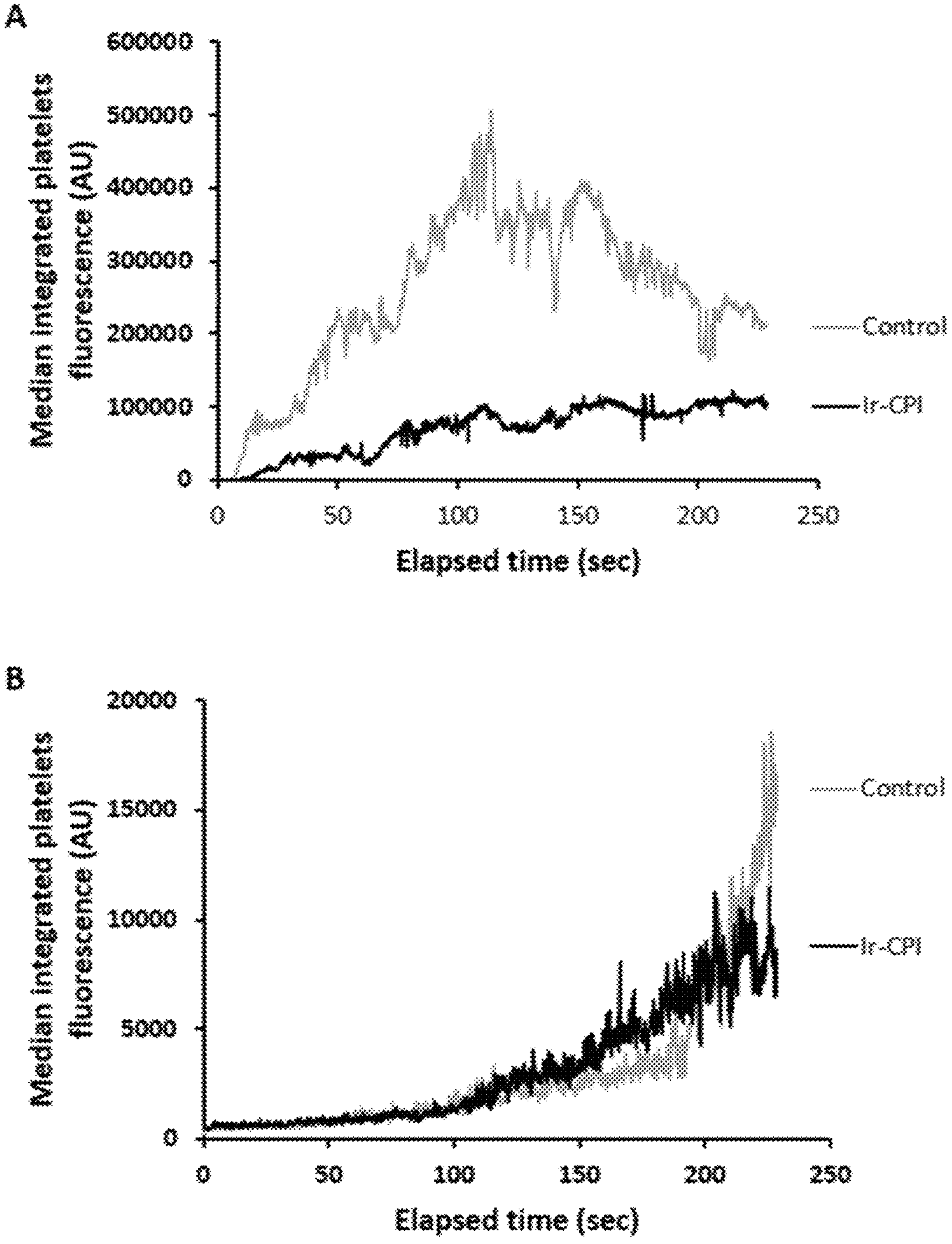
FIG. 1 is a combination of graphs showing the in vivo detection of platelets (A) and fibrin (B) after thrombus formation was induced in mice by vessel wall injury. Fibrin and platelets were detected using an Alexa Fluor 488-conjugated anti-fibrin antibody and a DyLight649-labeled anti-GPIb antibody, respectively. The median of integrated fluorescence over time (short time period) is presented for 53 (control) and 54 (Ir-CPI) thrombi generated in 5 mice per group. AU: arbitrary units.

The present invention is further illustrated by the following examples.

Example 1: Model Involving the Activation of the Extrinsic Coagulation Pathway

Materials and Methods

Material

Test Substance

Ir-CPI (MW=7660 Da) was obtained from Bachem (powder, batch 1060411, purity: 98.4%) and stored at −80° C. until use.

Ir-CPI was freshly prepared on the testing day by dissolution in NaCl 0.9% to reach the concentration of 50 mg/mL (corresponding to the maximal concentration to reach to avoid solubility issues).

NaCl 0.9% was used as a control.

Animals

Male mice (C57BL/6JRj) purchased from Janvier LABS were used for this study (5 to 8 weeks old).

Methods

Administration

Ir-CPI was administered intravenously as a bolus (20.5 mg/kg) immediately followed by a continuous infusion at a rate of 3.7 mg/kg/h (see Table 1 below). Due to fast distribution and elimination of Ir-CPI in the mice ($t1/2\alpha$=14 min and $t1/2\beta$=236 min), the combination of the bolus and the infusion was chosen in order to maintain a constant Ir-CPI concentration into the blood.

TABLE 1

Experiment set-up

| Model | n | Test item | Dose bolus (mg/kg) | Dose infusion (mg/kg/h) | Time of monitoring |
|---|---|---|---|---|---|
| Laser injury (platelet + fibrin detection) | 5 | Control (NaCl 0.9%) | — | — | 3.8 min (228 sec) |
| | 5 | Ir-CPI | 20.5 | 3.7 | 3.8 min (228 sec) |
| Laser injury (kinetics of fibrin generation) | 9 | Control (NaCl 0.9%) | — | — | 90 min |
| | 9 | Ir-CPI | 20.5 | 3.7 | 90 min |
| Laser injury (platelets + polymor-phonuclear neutrophils) | 4 | Control (NaCl 0.9%) | — | — | 4.5 min (270 sec) |
| | 4 | Ir-CPI | 20.5 | 3.7 | 4.5 min (270 sec) |
| Laser injury (assessment of neutrophil elastase activity) | 3 | Control (NaCl 0.9%) | — | — | 4.3 min (260 sec) |
| | 4 | Ir-CPI | 20.5 | 3.7 | 4.3 min (260 sec) |

n = number of mice used.

Intravital Microscopy of the Cremaster Muscle Microcirculation

Intravital video-microscopy of the cremaster muscle microcirculation was done as previously described (Falati et al., 2002).

Mice were anesthetized with intraperitoneal injection of ketamine (125 mg/kg), xylazine (12.5 mg/kg) and atropine (0.25 mg/kg) and were maintained at 37° C. on a thermo-controlled rodent blanket.

A tracheal tube was inserted into the trachea to facilitate breathing. A canula was inserted into a jugular vein for administration of pentobarbital. Pentobarbital (12 mg/kg) was administered in the jugular vein every 20-30 minutes to maintain the mice under anesthesia throughout the handling. The same jugular vein canula was used for the administration of the antibodies and the enzymatic substrate coupled to a fluorochrome that is necessary to follow the development of the thrombus (detection of fibrin and/or platelets and/or neutrophils and/or neutrophil elastase activity). A canula was also inserted in the second contralateral jugular vein for administration of the vehicle or the test item (Ir-CPI or NaCl).

After the scrotum was incised, the testicle and surrounding cremaster muscle were exteriorized onto an intravital microscopy tray. The cremaster muscle was continuously perfused with thermo-controlled (37° C.) and aerated (95% $N_2$, 5% $CO_2$) bicarbonate-buffered saline solution throughout the experiment.

Microvessel data were obtained using an Olympus AX61WI microscope with a 60×0.9-numerical aperture water immersion objective. The digital wide-field fluorescence microscopy system has previously been described (Falati et al., 2002). Digital images were captured with a Cooke Sensicam CCD camera in 640×480 format.

Laser-Induced Injury

Vessel wall injury was induced with a Micropoint Laser System (Photonics Instruments) focused through the microscope objective, parfocal with the focal plane and aimed at the vessel wall, as previously described (Dubois et al., 2006). Typically, 1 or 2 pulses were required to induce vessel wall injury.

Multiple thrombi were studied in a single mouse, with new thrombi formed upstream of earlier thrombi to avoid any contribution from thrombi generated earlier in the animal under study. Laser-beam injuries were done at various time after the start of test-item administration (+5 min up to about 150 min after bolus administration of Ir-CPI or NaCl (control)).

Image analysis was performed using Slidebook 4.1 (Intelligent Imaging Innovations). Fluorescence data were captured digitally at up to 50 frames per second and analyzed as previously described (Falati et al., 2002). The kinetics of thrombus formation were analyzed by determining median fluorescence values over time in a minimum number of 20 thrombi.

After the procedure, mice were euthanized with an overdose of pentobarbital (120 mg/kg).

Detection of Fibrin, Platelets, PMNs and Neutrophil Elastase Activity In Vivo

In vivo detection of fibrin was performed using an Alexa Fluor 488-conjugated anti-fibrin antibody from Darbousset et al., 2014, administered intravenously at 0.5 μg/g of mouse.

In vivo detection of platelets was performed using a DyLight649-labeled anti-GPIb antibody from Emfret, administered intravenously at 0.5 μg/g of mouse.

Detection of PMNs in vivo was performed using PE-labelled anti-Ly6G antibody.

In vivo detection of neutrophil elastase activity was performed using BODIPY-FL-labeled DQ-elastin conjugate fragment from Life Technologies, administered intravenously at 0.3 μg/g of mouse.

Blood Sampling and Plasma Preparation

At the end of the experiment (about 150 min after bolus administration), blood was collected from the inferior vena cava and was placed in 0.109 M 3.2% sodium citrate tubes (citrate/blood, v/v 1/9). Plasma (around 250 μL) was centrifuged at 18-22° C./at 2500 g during 15 min. Plasma was centrifuged again (18-22° C. at 2500 g during 15 min) and was stored into a polypropylene tube at −80° C. Plasma samples were later sent frozen on dry ice for dosage of the circulating concentration of Ir-CPI by ELISA.

Quantification of Ir-CPI in Plasma Samples

The quantification of circulating Ir-CPI in the plasma samples was assessed by ELISA at Eurofins, ADME Bioanalyses (Vergèze, France). A sandwich immuno-assay was carried out using two anti-Ir-CPI antibodies. The capture monoclonal antibody (Ir-CPI3) was coated to microtitration plates (Nunc, ThermoFischer Scientific, USA) at 1 μg/mL overnight at 4° C. in PBS (Hyclone, USA). Wells were blocked with PBS BSA 2% (Sigma-Aldrich, USA) at room temperature (RT) for 1 h and were then washed. Samples were added into the wells and incubated for 2 h at RT. The biotinylated detection antibody (L39-biotin), previously diluted in PBS BSA 1% (Sigma-Aldrich, USA), was added to the wells and complemented with streptavidin-HRP (REF) diluted in PBS BSA 1%. TMB SureBlue (KPL, REF) and $H_2SO_4$ 1N (VWR, USA) were used for spectrophotometric detection (450 nm).

Data Processing and Statistical Analysis

Data were expressed as median and inter-quartile ranges with associated sample size (n). Statistical comparison of data from Ir-CPI-treated groups versus those from the control group was conducted using a Mann-Whitney test (***p<0.001).

Results

The goal of the present study was to assess the antithrombotic efficacy of Ir-CPI in an experimental model of thrombosis in mice, wherein thrombosis was induced by a local injury of a cremaster muscle arteriole with a laser beam. This experimental model of thrombosis is thought to involve the activation of the extrinsic coagulation pathway leading to Tissue Factor-mediated thrombin generation (Dubois et al., 2007; Darbousset et al., 2012). Indeed, in such a model, the kinetics of thrombin formation and fibrin generation were reported to be drastically reduced in low Tissue Factor (TF) mice whereas the absence of factor XII ($FXII^{-/-}$ mice) had no effect (Darbousset et al., 2012). The laser-induced vessel wall injury model thus allows to assess the inhibitory effect of Ir-CPI on thrombosis involving the extrinsic coagulation pathway.

Monitoring of Platelet and Fibrin Accumulation After Laser Injury in Control and Ir-CPI-Treated Mice (Short-Time Period Measurement)

Platelet accumulation and fibrin generation on the injured vessel walls were monitored using the following fluorescently labeled antibodies: DyLight649-labeled anti-GPIb antibody and Alexa Fluor 488-conjugated anti-fibrin antibody, respectively.

Figure 2:
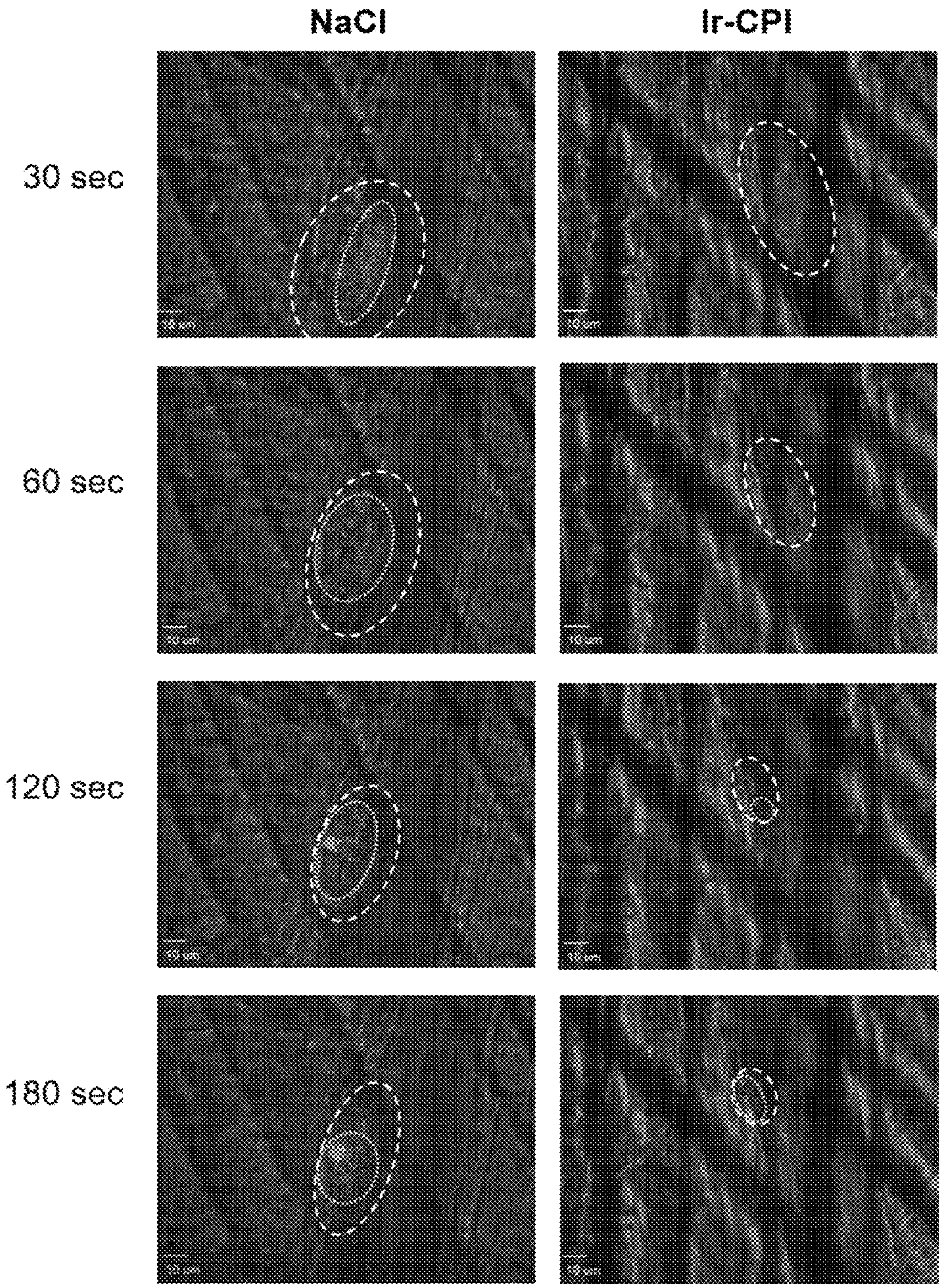
FIG. 2 is a combination of representative images of fluorescence microscopy taken in vivo 30, 60, 120 and 180 seconds after laser injury of a vessel wall inducing the formation of thrombus in mice treated with NaCl (control) or Ir-CPI. Fibrin and platelets were detected using an Alexa Fluor 488-conjugated anti-fibrin antibody and a DyLight649-labeled anti-GPIb antibody, respectively. Areas surrounded by a dashed line depict platelet accumulation and areas surrounded by a dotted line depict fibrin accumulation. Bars: 10 μm.

In control mice, platelets accumulated rapidly at the site of injury to reach a peak at about T114 sec (median of integrated platelet fluorescence: 508 541 AU) and, then, decreased until the end of the measurement period at T228 sec (median of integrated platelet fluorescence: 209 893 AU). Fibrin generation at the site of injury increased continuously until the end of the measurement period and the median of integrated fibrin fluorescence was 16 686 AU at T228 sec (FIG. 1 and FIG. 2).

In Ir-CPI-treated mice, the kinetics of platelet accumulation were different to those of control mice. Platelet accumulation was drastically decreased when compared to control mice. The maximal median of integrated platelet fluorescence measured was 121 783 AU at T214 sec. At T228 sec (i.e., the end of the measurement period), the median of integrated platelet fluorescence was 101 887 AU. Moreover, fibrin generation appeared to be less important in Ir-CPI-treated mice than in control mice during the first 3.8 min after laser injury. At T228 sec, the maximal median of integrated fibrin fluorescence was 7 539.7 AU (FIG. 1 and FIG. 2).

Mean plasma concentration measured in Ir-CPI-treated mice after about 150 min of procedure was 6.48±1.02 μg/mL (Mean±SEM; n=5).

Kinetics of Fibrin Generation After Laser Injury in Control and Ir-CPI-Treated Mice (Long-Time Period Measurement)

Figure 3:
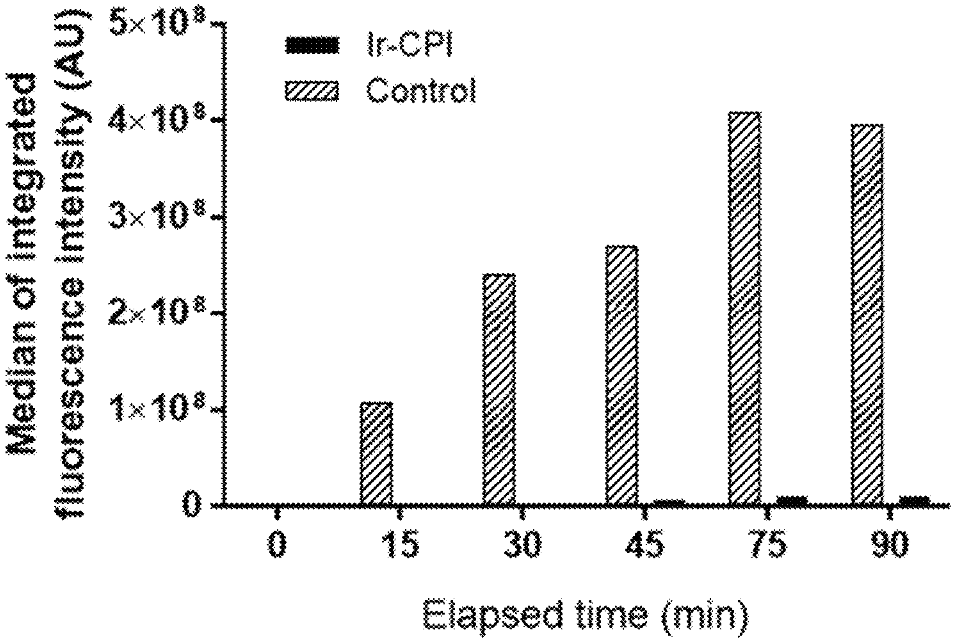
FIG. 3 is a graph showing the in vivo detection of fibrin during a 90 minute-elapsed time after thrombus formation was induced in mice by vessel wall injury. Fibrin was detected using an Alexa Fluor 488-conjugated anti-fibrin antibody. The median of integrated fluorescence over time (long time period) is presented for 53 (control) and 50 (Ir-CPI) thrombi generated in 9 mice (n=9 mice per group). AU: arbitrary units.
Figure 4:
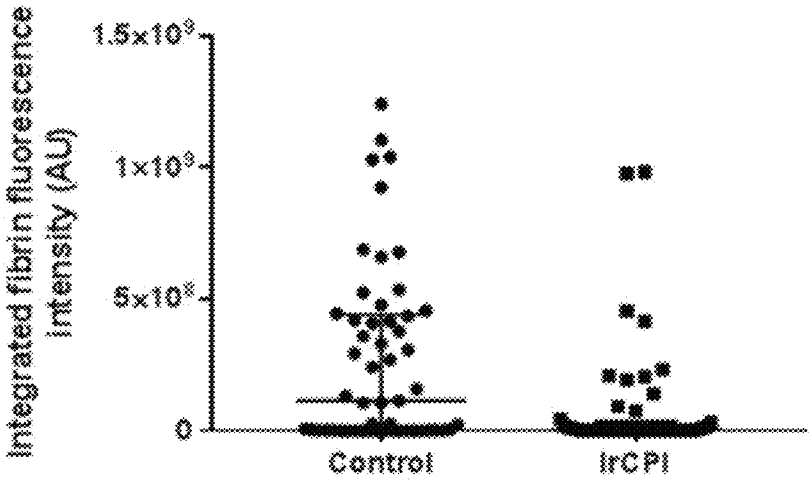
FIG. 4 is a graph showing the in vivo detection of fibrin during a 90 minute-elapsed time after thrombus formation was induced in mice by vessel wall injury. Fibrin was detected using Alexa Fluor 488-conjugated anti-fibrin antibody. Medians with inter-quartile ranges are presented for the control (n=53 thrombi) and Ir-CPI-treated mice (n=50 thrombi) generated in 9 mice (n=9 mice per group). AU: arbitrary units.

The kinetics of fibrin generation were measured during 90 min after vessel wall laser injury in control and Ir-CPI-treated mice. At every time point measured (0, 15, 30, 45, 75 and 90 min), the median of integrated fibrin fluorescence intensity was lower in Ir-CPI-treated mice than in control mice (FIG. 3 and FIG. 4).

Effect of Ir-CPI on Neutrophil Accumulation

It was demonstrated that polymorphonuclear neutrophils (PMNs) are the first cells to accumulate to the vessel wall following a laser-induced injury. Interactions of PMNs with activated endothelial cells is required for the initiation of thrombus formation (Darbousset et al., 2012).

Figure 5:
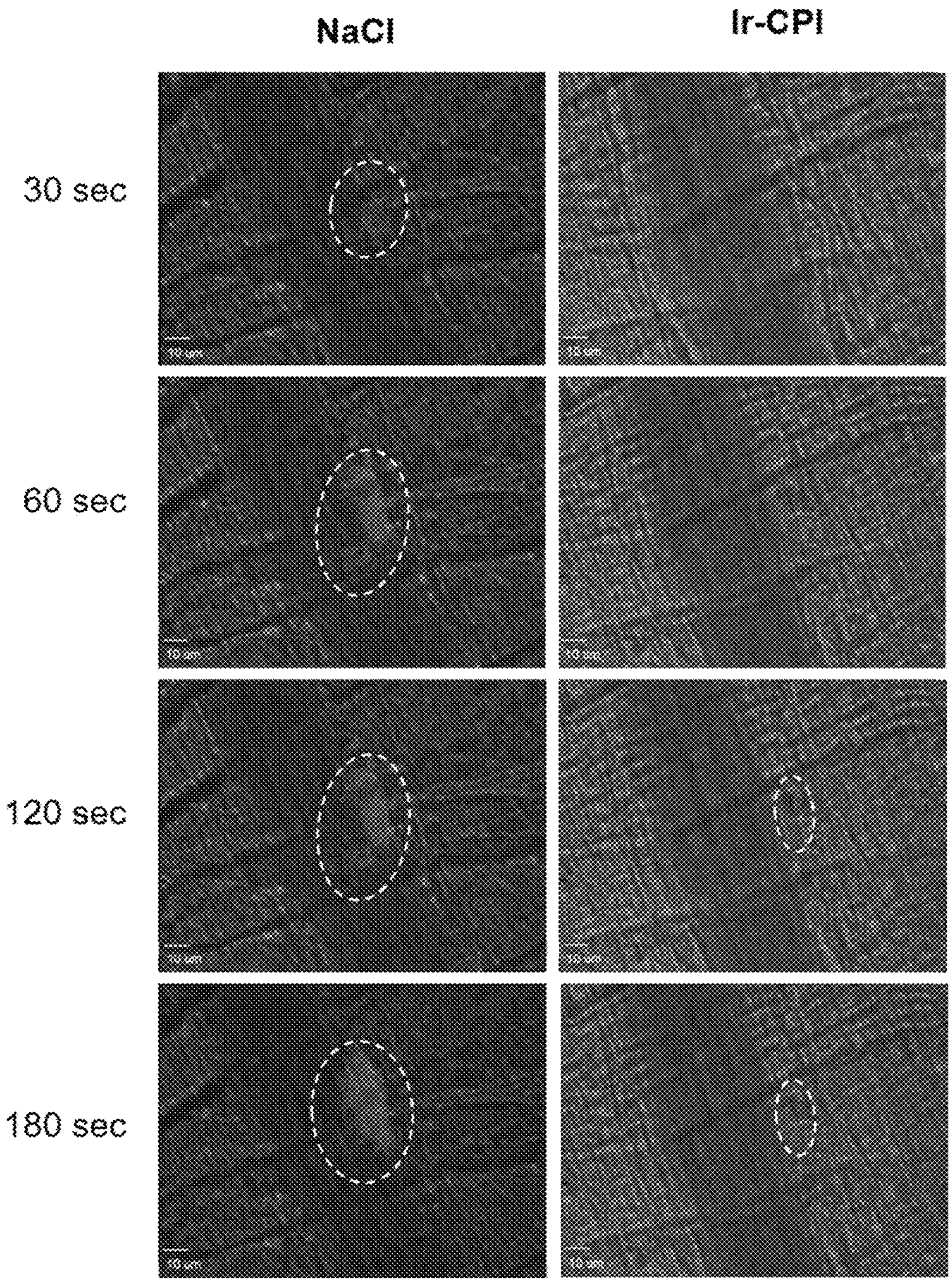
FIG. 5 is a combination of representative images of fluorescence microscopy taken in vivo 30, 60, 120 and 180 seconds after laser injury of a vessel wall inducing the formation of thrombus in mice treated with NaCl (control) or Ir-CPI. PMNs were detected using a PE-labelled anti-Ly6G antibody. Areas surrounded by a dashed line depict PMN accumulation. Bars: 10 μm.

To determine whether Ir-CPI has an impact on the accumulation of PMNs at the site of injury, the accumulation of PMNs on the injured vessel wall was monitored using a PE-fluorescently labeled antibody directed against Ly6G (FIG. 5).

Figure 6:
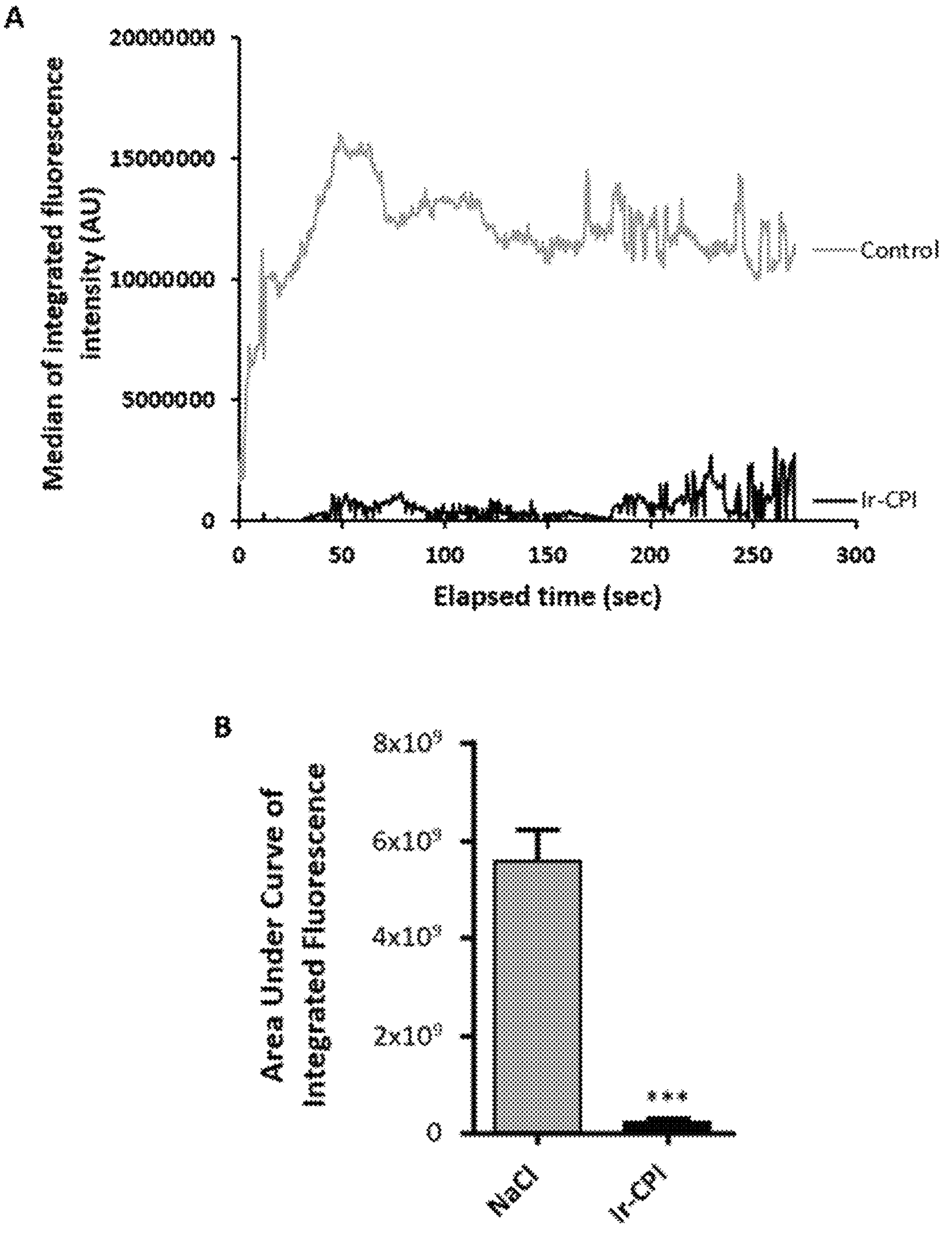
FIG. 6 is a combination of graphs showing the in vivo detection of PMNs after thrombus formation was induced in mice by vessel wall injury. PMN accumulation was assessed by using a PE-labeled anti-Ly6G antibody. The median of integrated fluorescence over time (A) and the corresponding area under curve (B) are presented for 26 (control) or 27 (Ir-CPI) thrombi generated in 8 mice (n=4 mice per group). AU: arbitrary units. A Mann-Whitney test was used for statistical analysis (*** $p<0.001$).

In control mice, PMNs accumulated rapidly at the site of injury to reach a peak at T 42 sec (median of integrated platelet fluorescence: $1.60\times10^7$ AU). Median of integrated PMN fluorescence was $1.10\times10^7$ AU at T270 sec (FIG. 6).

Figure 7:
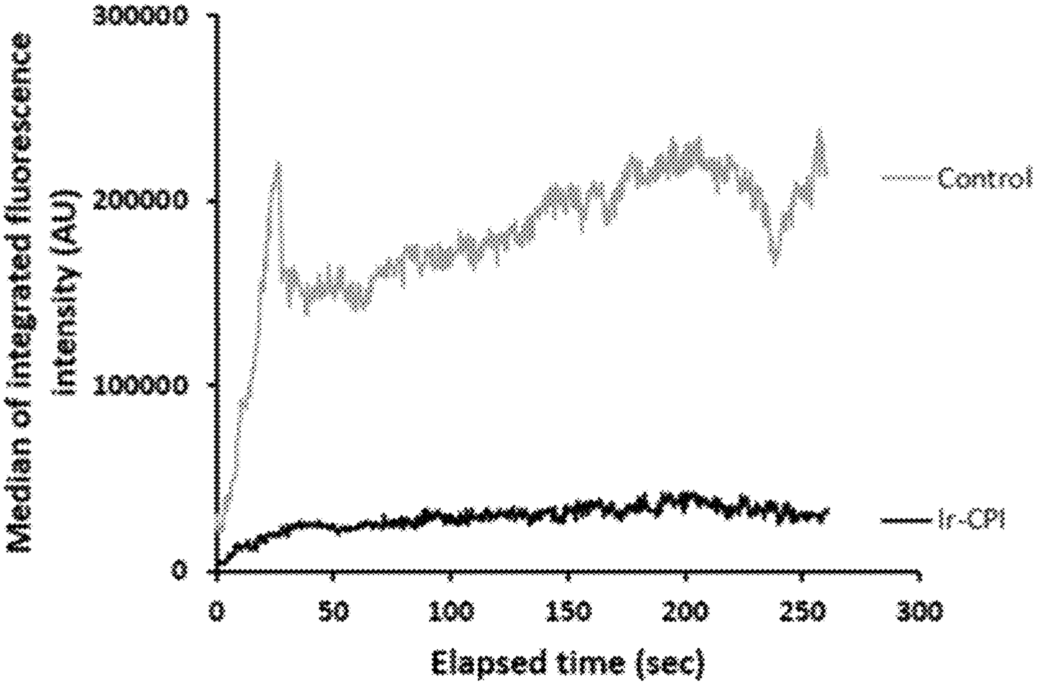
FIG. 7 is a graph showing the in vivo detection of neutrophil elastase activity after thrombus formation was induced in mice by vessel wall injury. Neutrophil elastase activity was assessed by using a BODIPY-FL-labeled DQ-elastin conjugate fragment as fluorescently labeled substrate of elastase. The median of integrated fluorescence over time is presented for 31 (control) or 23 (Ir-CPI) thrombi generated in 7 mice (n=3 for control mice and n=4 for Ir-CPI-treated mice). AU: arbitrary units.

In Ir-CPI-treated mice, the kinetics of neutrophil accumulation were different to those of control mice. Indeed, during the first 4.5 min after laser injury, PMN accumulation was drastically decreased when compared to control mice. The maximal median of integrated platelet fluorescence measured was $3.02\times10^6$ AU at T 261 sec. At T 270 sec (i.e., the end of the measurement period), the median of integrated PMN fluorescence was $2.78\times10^6$ AU (FIG. 6). Similar results were obtained when using a fluorescently labeled substrate of elastase as a marker of the activity of the PMNs. The signal corresponding to neutrophil elastase activity was drastically reduced in Ir-CPI-treated mice when compared to control mice (FIG. 7).

Conclusion

Taken together, these results demonstrate that Ir-CPI is unexpectedly active in an experimental model that is known to involve the activation of the extrinsic coagulation pathway. These results indicate that Ir-CPI exerts antithrombotic effects that are not necessarily associated to its known targets (i.e. Factors XIa and XIIa). Surprisingly, Ir-CPI inhibits at the site of lesion not only the formation of fibrin but also the accumulation of platelets, and even the earlier appearance of PMNs known to play an important role in the activation of the extrinsic coagulation system as they are the main source of TF required for thrombus formation at the site of laser injury (Darbousset, Thomas et al. 2012).

Example 2: In Vitro Platelet Aggregation Assay

Materials and Methods

Blood from healthy human donors, who had not taken anti-platelet agents within the 15 days prior to collection, was collected in citrated tubes and centrifuged for 13 min at 200 g. The platelet-rich plasma was collected and centrifuged for 13 min at 900 g in Tyrode buffer (138 mM NaCl, 2.9 mM KCl, 12 mM $NaHCO_3$, 5.5 mM glucose, 1.8 mM $CaCl_2$ and 0.4 mM $MgCl_2$, pH 7.4) containing 0.2% BSA, apyrase 0.02 U/mL and $PGI_2$ 500 nM. Washed platelets were resuspended in the Tyrode/BSA 0.2%/apyrase/$PGI_2$ solution and centrifuged at 900 g for 13 min. Platelets were resuspended in a Tyrode/BSA 0.2% solution at a concentration of $3.10^8$ platelets/mL. Platelets were kept at 37° C. for 30 min in a solution containing 4 μM of calcium and 6 μM of magnesium. Next, platelets were incubated at 37° C. under agitation for 5 to 10 minutes in an aggregometer APACT 4004 with ADP (adenosine diphosphate), TRAP (Thrombin Receptor-Activating Peptide) and/or Ir-CPI.

Results

The effect of Ir-CPI on platelet aggregation was assessed in vitro by using isolated human washed platelets (n=1).

Washed platelets were first either incubated with ADP (adenosine diphosphate), an activator of platelets that does not induce platelet aggregation, or with TRAP (Thrombin Receptor Activating Peptide), an activator of platelet aggregation. As expected and as shown in Table 2 below, ADP did not induce platelet aggregation (max aggregation: 6.9%) while TRAP activated platelet aggregation (max aggregation: 58.6 to 59.5%).

TABLE 2

Analysis of the effect of Ir-CPI on human washed platelet aggregation

| Condition | Comments | Aggregation Max (%) | Aggregation Slope (%/min) | Aggregation Latency (sec) |
|---|---|---|---|---|
| TRAP 20 μM | — | 59.5 | 33.1 | 41.0 |
| TRAP 20 μM + Ir-CPI 500 μg/100 μL | TRAP and Ir-CPI injected together | 71.8 | 35.1 | 98.6 |
| Ir-CPI 500 μg/100 μL + TRAP 20 μM | Ir-CPI injected alone and then TRAP injected at about 230 sec | 73.5 | 31.1 | 231.2 |
| TRAP 20 μM | — | 58.6 | 32.4 | 75.4 |
| Ir-CPI 500 μg/100 μL | — | 4.1 | 16.2 | 70.0 |
| ADP 20 μM | — | 6.9 | 19.4 | 51.8 |

Addition of Ir-CPI to washed platelets did not activate platelet aggregation (max aggregation: 4.1%). The addition of both Ir-CPI and TRAP to washed platelets did not significantly modify platelet aggregation (max aggregation: 71.7%) when compared to the positive control condition (TRAP alone: max aggregation: 58.6-59.5%). The effect was similar but presented a longer latency period (231.2 sec) when TRAP was added to Ir-CPI (max aggregation: 73.5%) (Table 2).

The results of Example 1 showed that Ir-CPI inhibits platelet accumulation in vivo. However, Ir-CPI does not inhibit platelet aggregation in an in vitro platelet aggregation assay. Taken together, these results suggest that Ir-CPI may act on another target than platelets, involved in thrombus formation.

In the laser-induced vessel wall injury model, polymorphonuclear neutrophils (PMNs) are known to adhere to injured vessels in the seconds after the lesion, preceding platelets, by binding to the activated endothelium. PMNs, by binding to the vessel wall, are the main source of blood-borne TF in the early phase of thrombus formation (Darbousset et al., 2012). The interaction of PMNs with endothelial cells is a critical step preceding platelet accumulation for thrombosis initiation.

The results of Example 1 show that Ir-CPI decreased PMN recruitment to the injured vessel wall. A reduction of neutrophil elastase activity was also detected under treatment with Ir-CPI. However, this reduction of elastase activity might result from the reduction in the number of neutrophils that have been recruited at the site of the lesion.

Example 3: Model of Cancer-Associated Thrombosis

Materials and Methods

Material

Test Substance

Ir-CPI (MW=7660 Da) was obtained from Bachem (powder, batch 1060411, purity: 98.4%) and stored at −80° C. until use.

Ir-CPI was freshly prepared on the testing day by dissolution in NaCl 0.9% to reach the concentration of 50 mg/mL (corresponding to the maximal concentration to reach to avoid solubility issues).

NaCl 0.9% was used as a control.

Animals

Male mice (C57BL/6JRj) purchased from Janvier LABS were used for this study (5 weeks old).

Methods

Administration

Ir-CPI was administered as indicated hereinabove (see Example 1) and as summarized in Table 3 below.

TABLE 3

Laser injury experiment set-up

| Model | n | Test item | Dose bolus (mg/kg) | Dose infusion (mg/kg/h) | Time of monitoring |
|---|---|---|---|---|---|
| Laser injury + cancer model (High dose of Ir-CPI) | 5 | Control cancer (NaCl 0.9%) | — | — | 4.6 min (278 sec) |
| | 4 | Ir-CPI cancer | 20.5 | 3.7 | 4.6 min (278 sec) |
| | 5 | Control WT (NaCl 0.9%) | — | — | 4.6 min (278 sec) |
| Laser injury + cancer model (Low dose of Ir-CPI) | 6 | Control cancer (NaCl 0.9%) | — | — | 4.2 min (250 sec) |
| | 5 | Ir-CPI cancer | 10.3 | 1.9 | 4.2 min (250 sec) |
| | 3 | Control WT (NaCl 0.9%) | — | — | 4.2 min (250 sec) |

n = number of mice used;
WT (Wild-Type) corresponds to cancer-free mice.

TABLE 4

Tail bleeding time experiment set-up

| Model | n | Test item | Dose bolus (mg/kg) | Dose infusion (mg/kg/h) |
|---|---|---|---|---|
| Bleeding time assessment | 8 | Control WT | — | — |
| | 7 | Ir-CPI Low dose WT | 10.3 | 1.9 |
| | 7 | Ir-CPI High dose WT | 20.5 | 3.7 |
| | 7 | Control cancer | — | — |
| | 7 | Ir-CPI Low dose cancer | 10.3 | 1.9 |
| | 7 | Ir-CPI High dose cancer | 20.5 | 3.7 |

n = number of mice used;
WT (Wild-Type) corresponds to cancer-free mice.

Induction of Ectopic Tumor

Murine Panc02 cells (mouse pancreatic ductal adenocarcinoma cell line) were cultured to a 80% confluence in RPMI-1640 medium (Life Technologies) supplemented with 10% FCS (PAA), 1000 U/mL penicillin (Life Technologies), 100 μg/mL streptomycin (Life Technologies) and 0.1% fungizone (Life Technologies) at 37° C. in a humidified atmosphere with 5% $CO_2$. Once in the exponential growth phase, cells were washed three times with PBS and briefly exposed to non-enzymatic cell dissociation buffer (Life Technologies) to dislodge the cells. The cells were carefully washed three times, resuspended in PBS, and diluted to the desired concentration.

Five-week-old C57BL/6 mice were injected subcutaneously in the right flank with a tumor cell suspension ($10^6$ cells in 100 μL of PBS). When the tumor became palpable (0.2 cm), measurements in two dimensions were performed with a caliper, and the volume of each tumor was calculated according to the formula for the volume of an ellipsoid: $\pi/6 \times a(b)^2$, where a is the largest diameter and b the smallest diameter of the tumor.

Intravital Microscopy of the Cremaster Muscle Microcirculation

Intravital video-microscopy of the cremaster muscle microcirculation was done as previously described (Falati et al., 2002) and as described hereinabove (see Example 1).

Laser-Induced Injury

Vessel wall injury was induced with a Micropoint Laser System (Photonics Instruments) as described hereinabove (see Example 1).

Platelet and fibrin accumulation after injury were monitored and detected as indicated hereinabove (see Example 1).

Tail Bleeding Time Assessment

Tail bleeding time assessment under NaCl or Ir-CPI treatment (Low or High dose) was performed as previously described (Mezouar et al., 2015) on anesthetized wild-type (i.e. cancer-free) or cancer-bearing mice. Briefly, a 1- to 3-mm portion of the distal tail was removed from mice; the tail was immersed in isotonic saline (37° C.), and the time to complete cessation of blood flow recorded. The bleeding time was monitored for a maximum of 10 min.

Data Processing and Statistical Analysis

For the tumor volume assessment, data were expressed as mean±SEM with associated sample size (n). For the assessment of Ir-CPI effect on platelet accumulation and fibrin generation in tumor-bearing mice, data were expressed as the median of integrated fluorescence over time. A Mann-Whitney test was used for statistical analysis and a One-way ANOVA with Tukey's multiple comparison test was used for the tail bleeding time.

Results

Using the same model of thrombosis induction, the antithrombotic effect of Ir-CPI was assessed in pancreatic cancer-bearing mice (ectopic model). Indeed, it was demonstrated that pancreatic cancer cells produce Tissue Factor (TF)-bearing microparticles (MP) playing a key role in thrombus formation in vivo (Thomas et al., 2009; Mezouar et al., 2015). Two doses (high dose and low dose) of Ir-CPI were tested in this model.

In another experiment, wild-type (cancer-free) and cancer-bearing mice, the time for tail bleeding to stop was assessed under NaCl (control) or Ir-CPI treatment (Low and High dose).

Assessment of Tumor Volume Before Laser Injury Experiments

Figure 8:
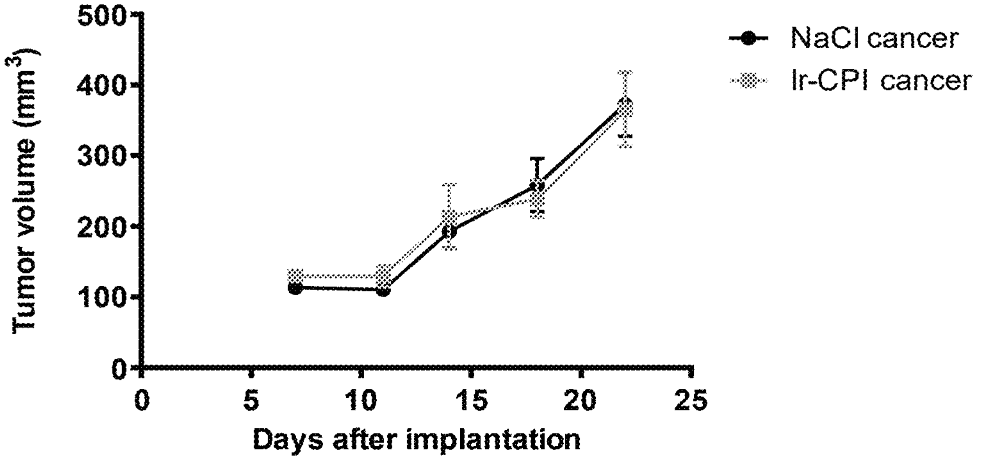
FIG. 8 is a graph showing the tumor volume after implantation of murine Panc02 cells in mice. Before the laser injury experiments, tumor volume was evaluated in mice bearing ectopic pancreatic tumors induced by Panc02 cells. In black, mice dedicated to control treatment, i.e., NaCl, (n=5) and in grey, mice dedicated to Ir-CPI treatment (n=4). Mean tumor volumes±SEM are represented.

In the mouse model of the study, cancer was induced by subcutaneous injection of mouse pancreatic (Panc02) cancer cells. Tumor-bearing mice were randomly divided into two groups (control and Ir-CPI). 22 days after the implantation of the Panc02 cells, mice from both groups received an injection of vehicle (NaCl (control)) or test-item (Ir-CPI) and were submitted to laser injuries of the cremaster muscle microcirculation for thrombus induction. As shown on FIG. 8, the mean tumor volume in the two groups was not statistically different at day 22 (control: 372.6±45.3 $mm^3$; n=5 and Ir-CPI: 365.0±52.1 $mm^3$; n=4). The latter mice were used for the experiment with High dose of Ir-CPI treatment. Mean tumor volume was also not statistically different in mice dedicated to the treatment with the Low dose of Ir-CPI (data not shown).

Monitoring of Platelet and Fibrin Accumulation After Laser Injury

Tumor-bearing mice were attributed to the Ir-CPI-treated group (Ir-CPI cancer) or to the control group (NaCl cancer). Moreover, cancer-free mice treated with NaCl (NaCl cancer-free) were also used as negative control. All mice were submitted to laser injuries in arterioles of the cremaster muscle to trigger thrombosis. Ir-CPI treated mice received either a low or a high dose of the investigative product.

Platelet accumulation and fibrin generation on the injured vessel walls were monitored using the following fluorescently labeled antibodies: DyLight649-labeled anti-GPIb antibody and Alexa Fluor 488-conjugated anti-fibrin antibody, respectively.

Figure 9:
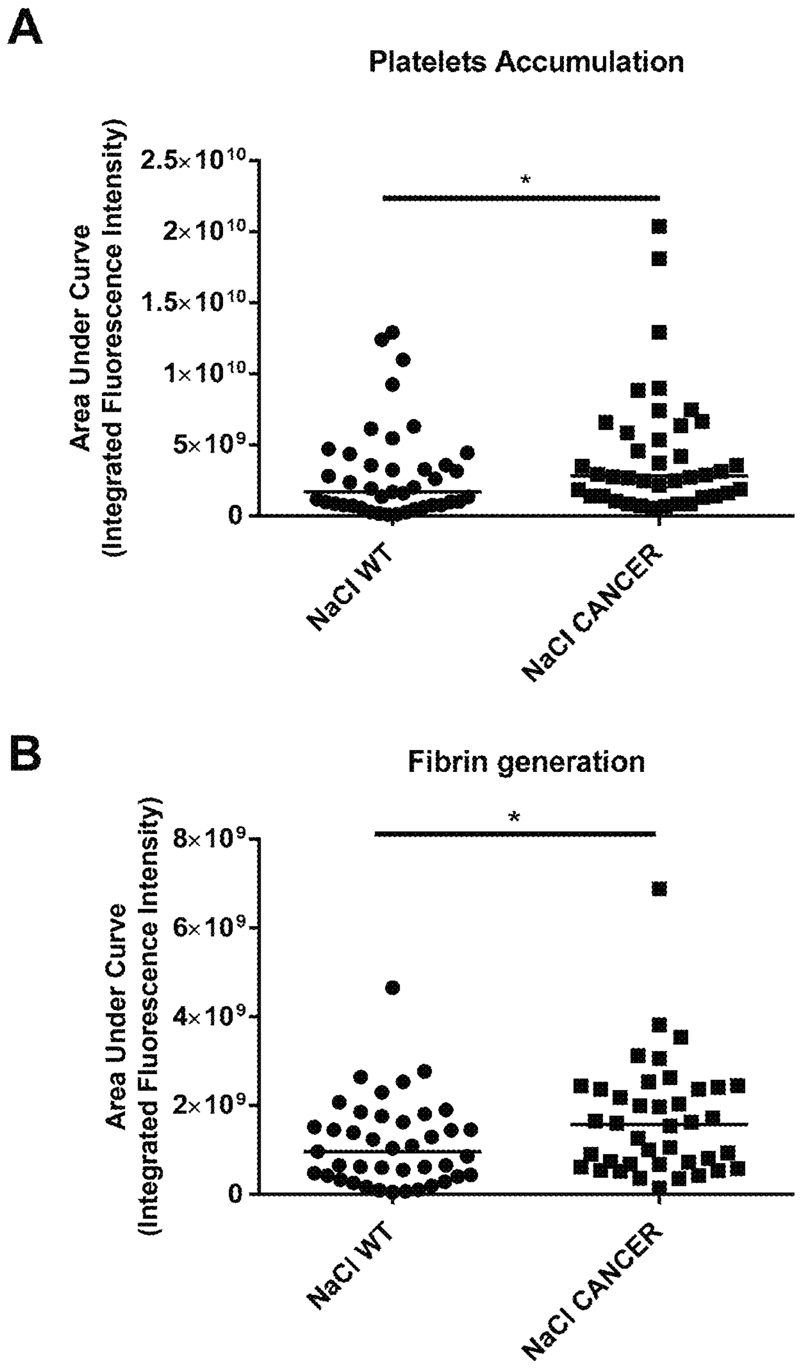
FIG. 9 is a combination of graphs showing the in vivo detection of platelets and the generation of fibrin after thrombus formation was induced in mice by vessel wall injury. Fibrin and platelets were detected using an Alexa Fluor 488-conjugated anti-fibrin antibody and a DyLight649-labeled anti-GPIb antibody. The area under curve of platelet (A) or fibrin integrated fluorescence intensity (B) is presented for 41 (NaCl WT, i.e. cancer-free; n=3 mice) or 40 (NaCl cancer; n=6 mice) thrombi generated. A Mann-Whitney test was used for statistical analysis (*p<0.05).
Figure 10:
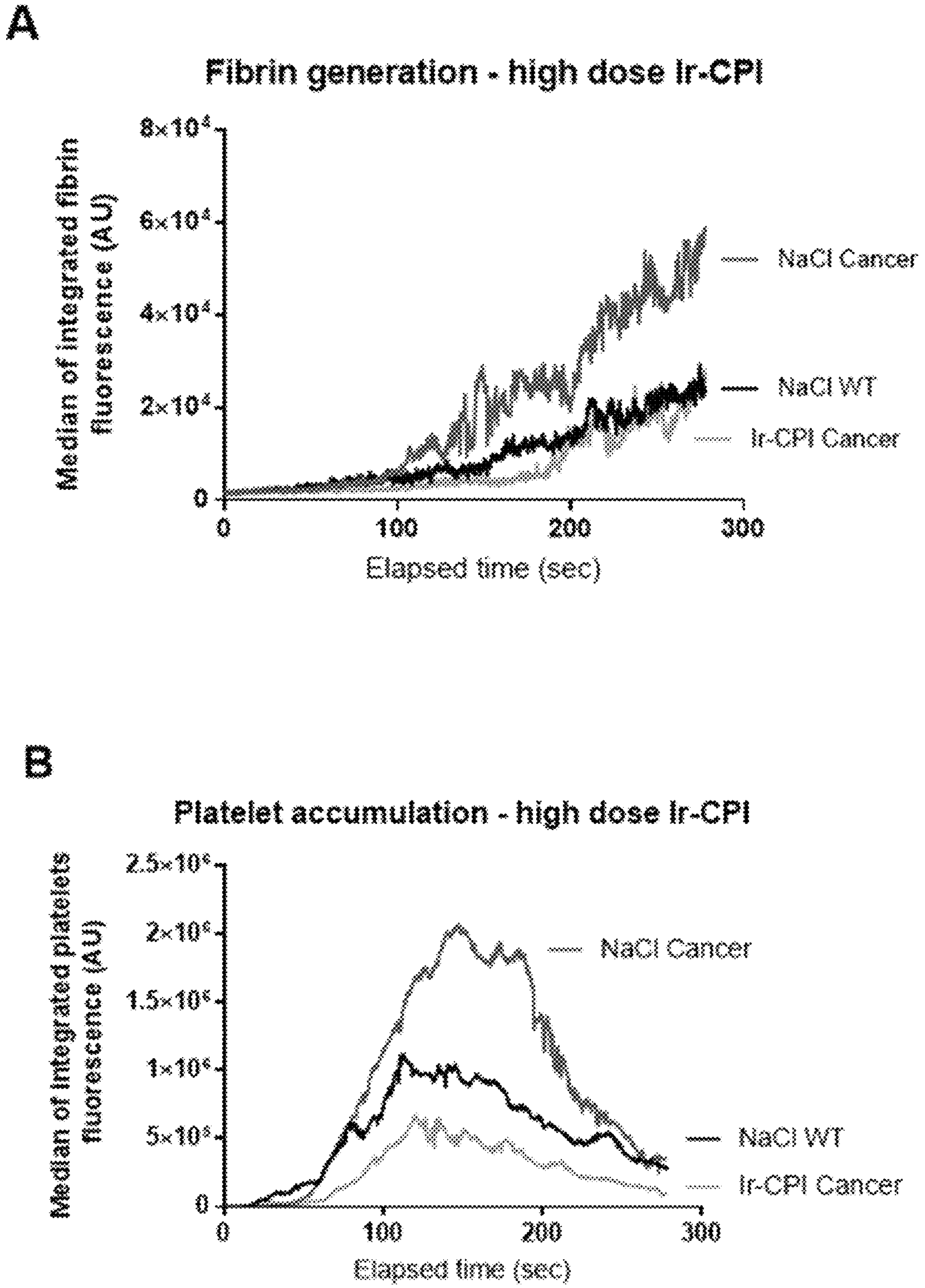
FIG. 10 is a combination of graphs showing the in vivo detection of fibrin (A) and platelets (B) after thrombus formation was induced in tumor-bearing mice by vessel wall injury in mice treated with 20.5 mg/kg (bolus)+3.7 mg/kg/h (infusion) (i.e. high dose). Fibrin and platelets were detected using an Alexa Fluor 488-conjugated anti-fibrin antibody and a DyLight649-labeled anti-GPIb antibody, respectively. The median of integrated fluorescence over time is presented for 44 (NaCl cancer-free, corresponding to the administration of NaCl to cancer-free mice), 34 (NaCl cancer, corresponding to the administration of NaCl to tumor-bearing mice) and 39 (Ir-CPI cancer, corresponding to the administration of Ir-CPI to tumor-bearing mice) thrombi generated in 14 mice (n=5 for NaCl cancer-free mice, n=5 for NaCl cancer mice and n=4 for Ir-CPI cancer mice). AU: arbitrary units.

NaCl cancer mice presented a prothrombotic state as assessed by the high accumulation of platelets and high amount of fibrin generation at the sites of injuries when compared to the NaCl cancer-free mice. Indeed, the integrated fluorescence intensity of platelet and fibrin labeling (area under curve) was significantly higher in control cancer mice when compared to control WT mice (*$p<0.05$). In the control cancer and control WT mice, the median of integrated fibrin fluorescence was 59 172 AU and 23 005 AU at T 278 sec, respectively (FIG. 9 and FIG. 10).

Figure 11:
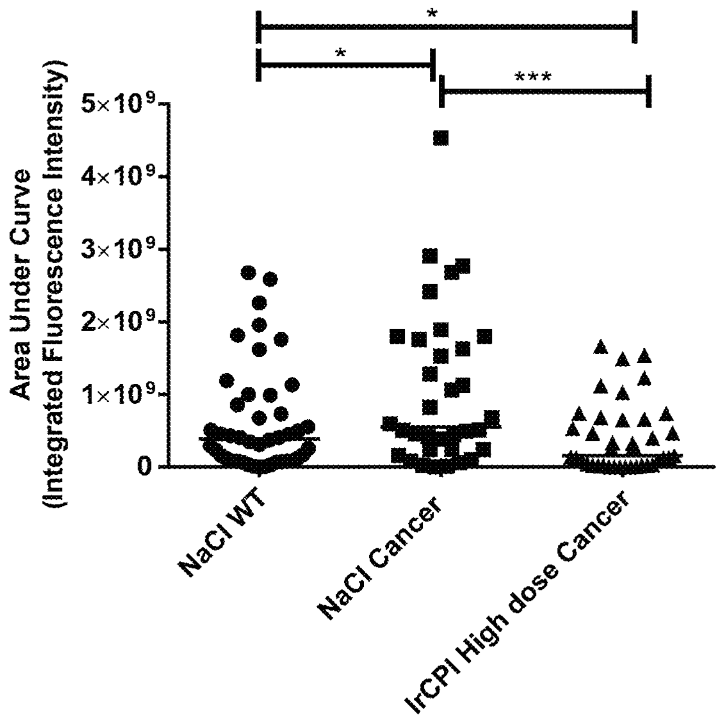
FIG. 11 is a graph showing the integrated fluorescence intensity of platelets (area under curve) presented for 44 (NaCl cancer-free mice), 34 (NaCl cancer mice) or 39 (Ir-CPI cancer mice) thrombi generated in 14 mice treated with high dose Ir-CPI (n=5 for NaCl cancer-free mice, n=5 for NaCl cancer mice; and n=4 for Ir-CPI cancer mice). Platelets were detected using a DyLight649-labeled anti-GPIb antibody. A Mann-Whitney test was used for statistical analysis (*p<0.05; ***p<0.001).
Figure 12:
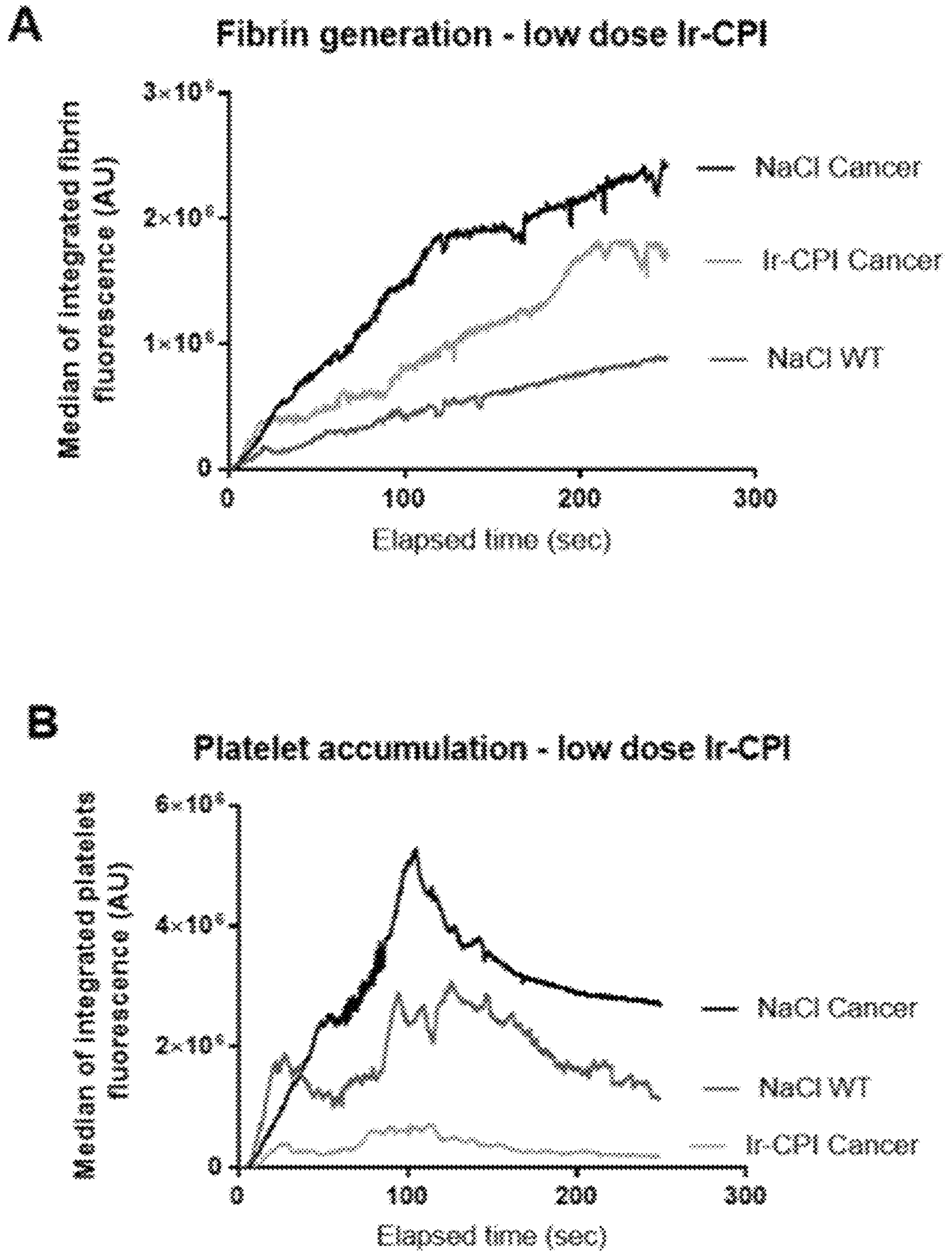
FIG. 12 is a combination of graphs showing the in vivo detection of fibrin (A) and platelets (B) after thrombus formation was induced in tumor-bearing mice by vessel wall injury in mice treated with 10.3 mg/kg (bolus)+1.9 mg/kg/h (infusion) (i.e. low dose). Fibrin and platelets were detected using an Alexa Fluor 488-conjugated anti-fibrin antibody and a DyLight649-labeled anti-GPIb antibody, respectively. The median of integrated fluorescence over time is presented for 41 (NaCl cancer-free, corresponding to the administration of NaCl to cancer-free mice), 40 (NaCl cancer, corresponding to the administration of NaCl to tumor-bearing mice) and 40 (Ir-CPI cancer, corresponding to the administration of Ir-CPI to tumor-bearing mice) thrombi generated in 14 mice (n=3 for NaCl cancer-free mice, n=6 for NaCl cancer mice and n=5 for Ir-CPI cancer mice). AU: arbitrary units.
Figure 13:
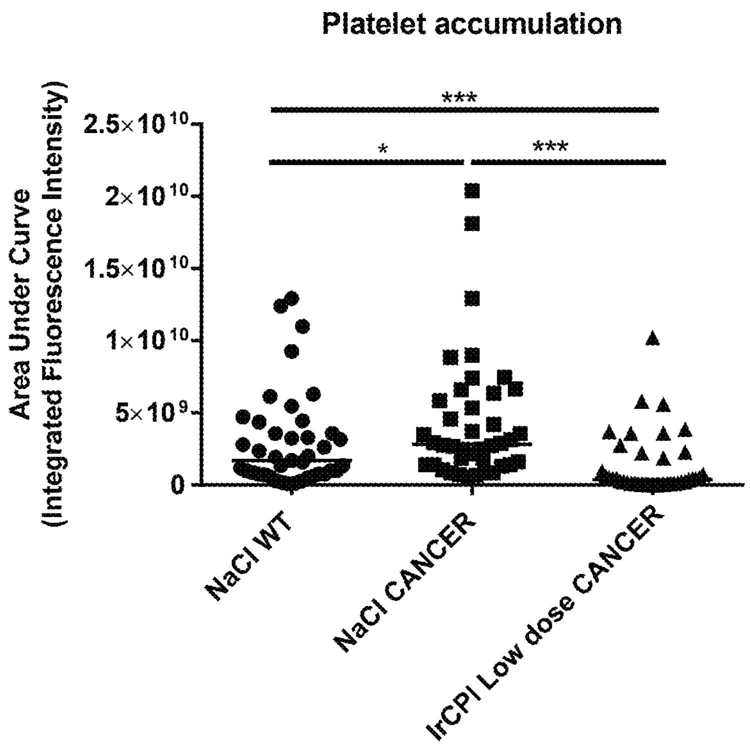
FIG. 13 is a graph showing the integrated fluorescence intensity of platelets (area under curve) presented for 41 (NaCl cancer-free mice), 40 (NaCl cancer mice) or 40 (Ir-CPI cancer mice) thrombi generated in 14 mice (n=3 for NaCl cancer-free mice, n=6 for NaCl cancer mice; and n=5 for Ir-CPI cancer mice). Ir-CPI cancer mice were treated with 10.3 mg/kg (bolus)+1.9 mg/kg/h (infusion) of Ir-CPI (i.e. low dose). Platelets were detected using a DyLight649-labeled anti-GPIb antibody. A Mann-Whitney test was used for statistical analysis (*p<0.05; ***p<0.001).

A significant decrease of platelet accumulation and fibrin generation was observed in both High dose and Low dose Ir-CPI-treated cancer mice when compared to the NaCl cancer mice. As shown in FIG. 11, the integrated fluorescence intensity of platelet labeling (area under curve) was significantly lower in High dose Ir-CPI-treated cancer mice than in NaCl cancer-free mice (*$p<0.05$) and NaCl cancer mice (*$p<0.001$). Similar results were obtained with Low dose Ir-CPI-treated mice (FIG. 12 and FIG. 13**).

Assessment of Tail Bleeding Time

Figure 14:
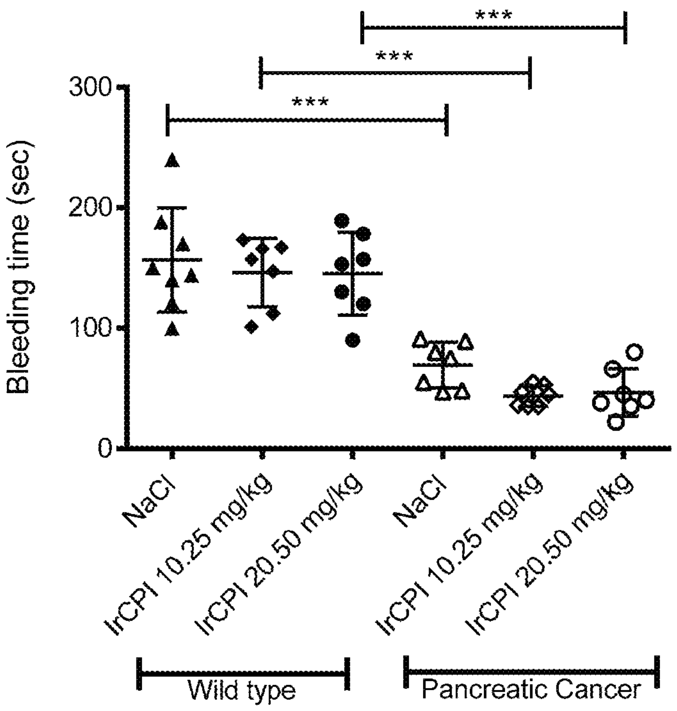
FIG. 14 is a graph showing bleeding times (in seconds) in NaCl wild-type (i.e. cancer-free) mice, in Ir-CPI-treated wild-type (i.e. cancer-free) mice (low and high dose) and in NaCl cancer-bearing mice or in Ir-CPI-treated cancer-bearing mice (low and high dose). A one-way ANOVA was used for statistical analysis (***p<0.001). All groups tested included 7 mice excepted for the NaCl wild-type mice group which included 8 mice.

Tail bleeding time was significantly reduced (*$p<0.001$) in mice developing a tumor (e.g. median time for NaCl treated-mice that received Panc02 cancer cells was 75 sec) in comparison with mice that did not (e.g. median time for wild-type (i.e. cancer-free) NaCl treated-mice was 147 sec) (FIG. 14). No significant effect of Ir-CPI treatment (Low and High dose) was observed on the tail bleeding time in cancer-free and in cancer-bearing mice, as compared to NaCl-treated mice (FIG. 14**).

Conclusion

The pathogenesis of the prothrombotic state in cancer is associated with the generation of a local and systemic hypercoagulable/thrombotic state that confers a growth advantage to tumor cells. It was demonstrated that pancreatic cancer cells produce tissue factor (TF)-bearing microparticles (MP) playing a key role in thrombus formation in vivo (Thomas et al., 2009; Mezouar et al., 2015). PMNs in mice with cancer have increased propensity to form neutrophil extracellular traps (NETs)-web-like structures formed by externalized chromatin and secreted proteases; a process called NETosis (Leal et al., 2017). Moreover, extracellular chromatin released through NET formation was demonstrated to be a cause for cancer-associated thrombosis (Demers et al., 2012; Mauracher et al., 2018).

The results of Example 3 show that Ir-CPI inhibits the prothrombotic state linked to cancer in the mouse model of laser injury. Indeed, in mice bearing an ectopic pancreatic tumor, Ir-CPI decreases significantly platelet accumulation and fibrin formation at the sites of laser injury. Importantly, in cancer-free and cancer-bearing mice, Ir-CPI has no effect on the tail bleeding time, showing that it does not impair hemostasis.

Example 4: NETosis Assay

Materials and Methods

Material

Neutrophils were isolated from the bone marrow of femurs of mice (C57BL/6) as previously described (Hu 2012) using FR-1-coupled magnetic beads (anti-Ly6G Microbead Kit, Miltenyi Biotec).

Methods

In Vitro NETosis Assay

Cells were harvested, centrifugated and incubated during 30 min with or without 2 ng/ml of TNFα in Hanks solution (Gibco). Neutrophils were seeded on slides coated with poly-L-lysine and incubated at 37° C. for 1 h in Hanks solution. Next, neutrophils were activated with or without 25 μM of platelet-activating factor (PAF)±Ir-CPI (0.65 or 2 μM) in Hanks solution (3 h at 37° C.). NET formation was assessed by immunofluorescence (fluorescent microscope from Leica) after fixation of neutrophils with 4% PAF (paraformaldehyde) and fluorescent labelling of citrullinated histones (H3 antibody) and nuclei (Hoechst). Processing and analysis of images was performed using the FIJI software.

Data Processing and Statistical Analysis

Percentage of NETosis (median) was presented for 5 independent experiments. A Wilcoxon test was used for statistical analysis (ns: not significant; *$p<0.05$; $p<0.01$; *$p<0.001$).

Results

Following the results of Example 3, the effect of Ir-CPI on the PMN activation state was assessed in vitro by assessing NET formation. Indeed, it was reported that PMNs in mice with cancer have increased propensity to form neutrophil extracellular traps (NETs) demonstrated to be a cause for cancer-associated thrombosis (Demers, Krause et al. 2012, Mauracher, Posch et al. 2018).

Effect of Ir-CPI on the NETosis In Vitro

It was reported that PMNs in mice with cancer have an increased propensity to form neutrophil extracellular traps (NETs), i.e., web-like structures formed by externalized chromatin and secreted proteases, a process called NETosis (Leal et al., 2017). Moreover, extracellular chromatin released through NET formation was demonstrated to be a cause for cancer-associated thrombosis (Demers et al., 2012; Mauracher et al., 2018).

Figure 15:
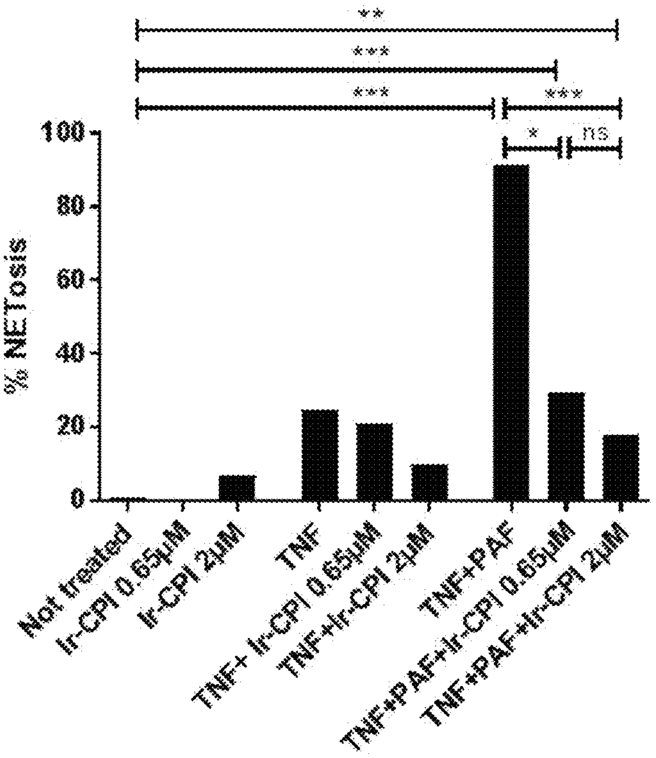
FIG. 15 is a graph comparing NETosis under different in vitro experimental conditions (untreated control, priming with tumor necrosis factor α (TNFα) with or without activation with platelet-activating factor (PAF), and/or incubation with Ir-CPI as indicated). The percentage of NETosis (median) was calculated after analyzing immunofluorescent staining and NET length (n=5 independent experiments; 5 random fields per condition were analyzed). A Wilcoxon test was used for statistical analysis (ns: not statistically significant; *p<0.05; p<0.01; *p<0.001).

To assess the effect of Ir-CPI on NETosis, immunofluorescent staining (Hoechst for DNA and H3Cit for citrullinated histones labeling) was performed on PMNs isolated from bone marrow of femurs of mice and submitted to different in vitro experimental conditions (untreated control, priming with TNFα with or without activation with PAF, and/or incubation with Ir-CPI) as shown on FIG. 15.

As positive control of NET formation, PMNs primed with TNFα and activated with PAF were used. These PMNs presented an increased percentage of NETosis when compared to untreated PMNs (*p<0.001), which validated the model (FIG. 15**).

As shown on FIG. 15, when PMNs were primed with TNFα, activated with PAF and incubated with Ir-CPI (0.65 and 2 μM), a significant reduction of the percentage of NET formation was observed when compared to PMNs incubated with TNFα and PAF (*p<0.05 for Ir-CPI at 0.65 μM and ***p<0.001 for Ir-CPI at 2 μM).

These results demonstrate that, in vitro, Ir-CPI reduces NETosis when incubated with activated neutrophils.

Example 5: Effect of Ir-CPI on Neutrophil Activation

Materials and Methods

Neutrophils were isolated from the bone marrow of femurs of mice (C57BL/6) as previously described (Hu 2012), using FR-1-coupled magnetic beads (anti-Ly6G Microbead Kit, Miltenyi Biotec). For activation with TFNα, cells were harvested, centrifugated and incubated during 30 min with or without 2 ng/ml of TNFα in Hanks solution (Gibco). Next, neutrophils were incubated with Ir-CPI (0.65 or 2 μM) in Hanks solution (1 h at 37° C.). For activation with ATP, cells were harvested, centrifugated and incubated with ATP 10 μM and Ir-CPI (0.65 or 2 μM) in Hanks solution (1 h at 37° C.). After washing of cells, expression of CD11b, activated CD11b or Ly6G was assessed by flow cytometry (Beckman Coulter Gallios). Antibodies used for neutrophil identification and activation analyses were IRR IgG1-FITC (irrelevant antibody), anti-CD45-APC, anti-Ly6G-PE and anti-CD11b-FITC or Alexa Fluor 647 anti-activated CD11b-. Analysis of results was performed using the Kaluza software (Beckman Coulter).

Data Processing and Statistical Analysis

Percentage of activation marker expression was presented as mean±SEM (n=3independent experiments for TNFα activation and n=2 independent experiments for ATP activation). For experiments with TNFα activation, a one-way ANOVA followed by a Tukey's multiple comparison test were used for statistical analysis (ns: not significant; *p<0.05).

Results

Following the results of Example 4, the effect of Ir-CPI on the PMN activation state was assessed in vitro by assessing the expression of neutrophil activation markers following incubation with molecules known to activate neutrophils, namely Adenosine Triphosphate (ATP) and Tumor Necrosis Factor α (TNFα).

ATP was shown to contribute to neutrophil activation leading to their adhesion at the site of laser-induced endothelial injury, a necessary step leading to the generation of fibrin, and subsequent platelet-dependent thrombus formation (Darbousset, Delierneux et al. 2014). Moreover, TNFα, another activator of neutrophils (Futosi, Fodor et al. 2013), was tested in this example.

Effect of Ir-CPI on Neutrophil Activation Following Incubation with TNFα

Figure 16:
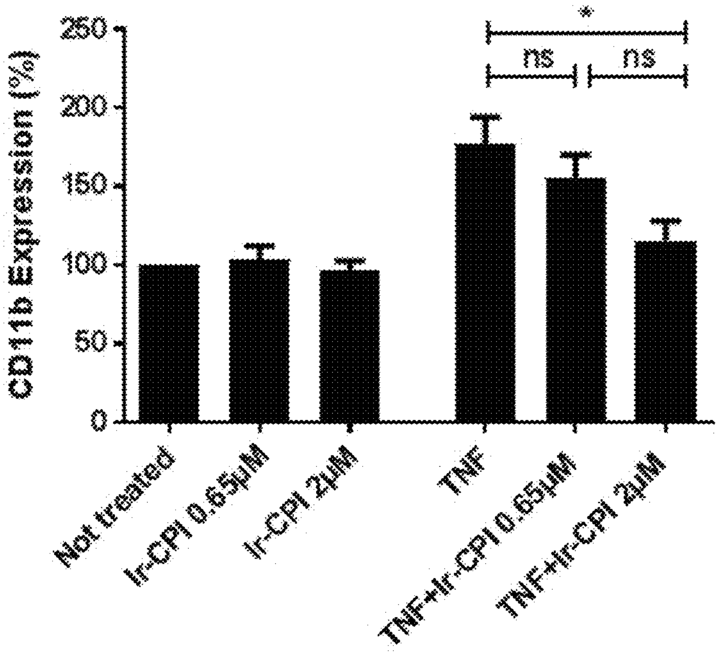
FIG. 16 is a graph comparing the expression of CD11b at the surface of neutrophils under different experimental conditions (untreated control, priming with TNFα and/or incubation with Ir-CPI as indicated). Data are presented as mean±SEM (n=3 independent experiments). A one-way ANOVA followed by a Tukey's multiple comparison test were used for statistical analysis (ns: not statistically significant; *p<0.05).

Neutrophils isolated from bone marrow of femurs of mice were submitted to different in vitro experimental conditions (untreated control, priming with TNFα and/or incubation with Ir-CPI) to assess the effect of Ir-CPI on their activation status. The activation status was assessed by analyzing the percentage of CD11b expression at the surface of neutrophils (FIG. 16).

Incubation of untreated neutrophils with Ir-CPI (0.65 and 2 μM) had no effect on the expression of CD11b. Neutrophils primed with TNFα were used as positive control of neutrophil activation. As shown on FIG. 16, neutrophils primed with TNFα presented an increased expression of CD11b when compared to untreated neutrophils. Strikingly, neutrophils primed with TNFα and incubated with Ir-CPI (2 μM) displayed a significant reduction of the CD11b expressed at their cell surface (*p<0.05).

These results demonstrate that Ir-CPI alters neutrophil activation induced by TNFα through a decreased CD11b expression in vitro.

Effect of Ir-CPI on Neutrophil Activation Following Incubation with ATP

Figure 17:
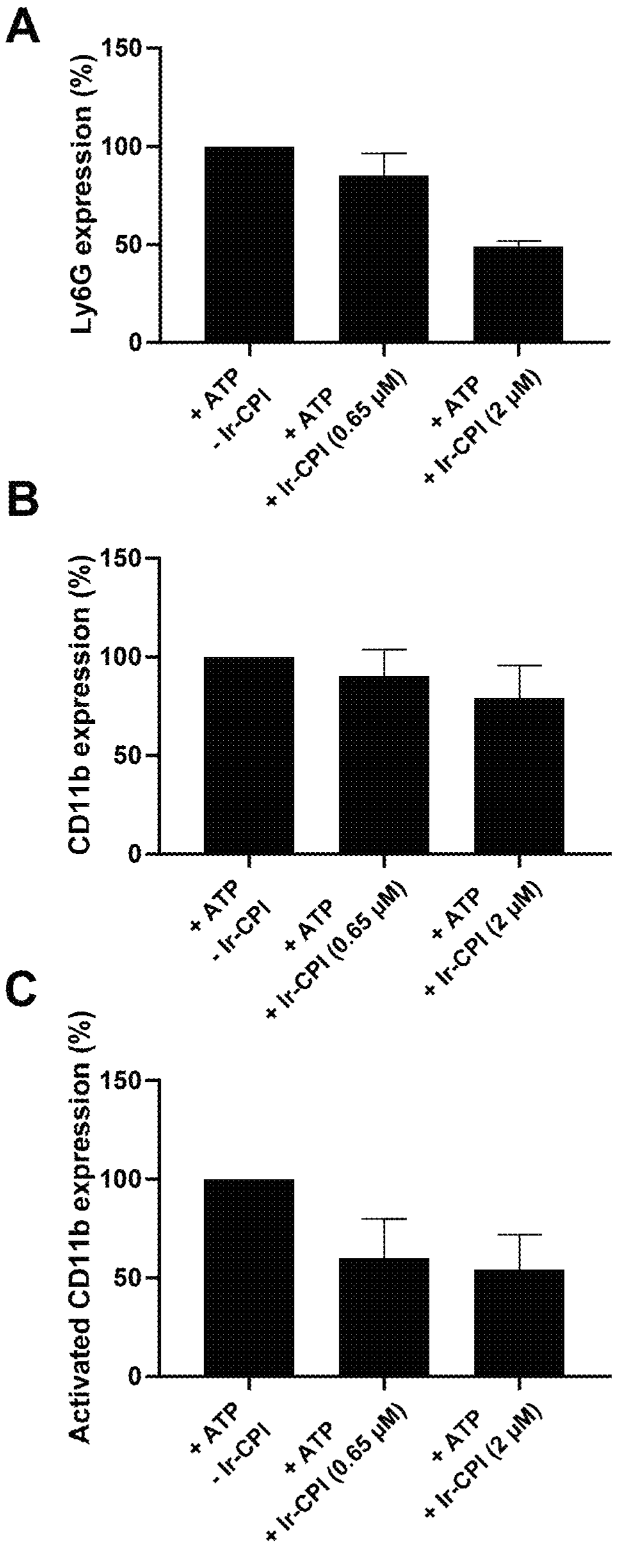
FIG. 17 is a graph comparing the expression of Ly6G (A), CD11b (B), and activated CD11b (C) at the surface of neutrophils under different experimental conditions (control activated by ATP, neutrophils incubated with Ir-CPI [0.65 or 2 μM] and activated with ATP). Data are presented as mean±SEM (n=2 independent experiments).

Neutrophils isolated from bone marrow of femurs of mice were submitted to different in vitro experimental conditions (untreated control or incubation with Ir-CPI, and with or without ATP) to assess the effect of Ir-CPI on their activation status. The activation status was assessed by analyzing the percentage of CD11b, activated CD11b and Ly6G expressions at the surface of neutrophils (FIG. 17).

Incubation of untreated neutrophils with Ir-CPI (0.65 and 2 μM) had no effect on the expression of CD11b (FIG. 17B). Nevertheless, Ir-CPI significantly decreased the expression of activated CD11b at the surface of neutrophils (FIG. 17C). The expression of Ly6G was also decreased at the surface of neutrophils when incubated with Ir-CPI (FIG. 17A).

These results demonstrate that, in vitro, Ir-CPI alters neutrophil activation induced by ATP through a decreased expression of activated CD11b.

Thus, Ir-CPI inhibits the thrombus formation following activation of the extrinsic coagulation pathway not through the inhibition of tissue factors specific of this pathway, such as Tissue Factor, but through the inhibition of neutrophil recruitment, activation and NETs formation. These events are the initial steps resulting in the activation of the extrinsic coagulation system and subsequent thrombus formation following laser endothelial injury.

Example 6: Absence of Interaction of Ir-CPI with the Zymogen Form of FXII

FXII circulates in the blood as an 80-kDa single-chain polypeptide zymogen with no enzymatic activity. When auto-activated due to a contact with polyanionic surfaces, FXII is converted into α-FXIIa by cleavage of the R353-V354 peptide bond. The resulting α-FXIIa has a heavy chain of 50 kDa, connected to a light chain of 28 kDa by the Cys340-Cys467 disulfide bridge. Plasma kallikrein further cleaves α-FXIIa at the peptide bonds R343-L344 and R334-N335 to give β-FXIIa (Davoine C. et al. 2020 European Journal of Medicinal Chemistry, Volume 208).

An assessment of the protein interaction between coagulation Factor XII (zymogenic form) and Ir-CPI and between coagulation Factor XIIa (activated form) and Ir-CPI was performed using an in silico structural analysis.

Materials and Methods

Modeling of the protein complexes were performed using AlphaFold2. Structural analysis was performed with ChimeraX and the DALI server.

Results

Figure 18A:
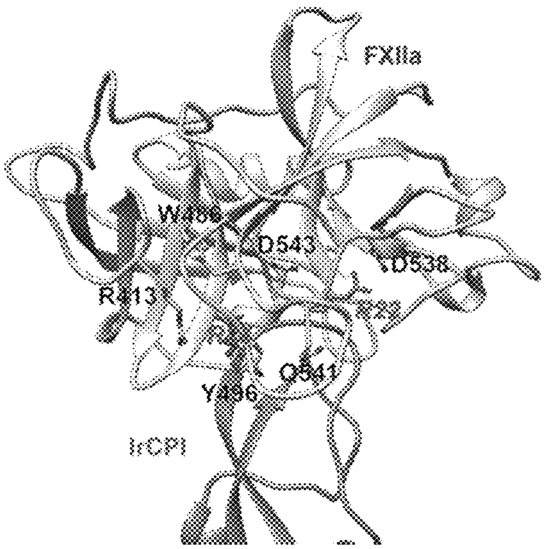
FIG. 18A-18B is a 3D projection scheme.

In the FXII zymogenic form, the substrate binding cavities S−1 and S+1 in the catalytic domain of FXII are disorganized and misaligned (FIG. 18A), which is incompatible for interactions with the key binding residues R24 and R22 of Ir-CPI.

Figure 18B:
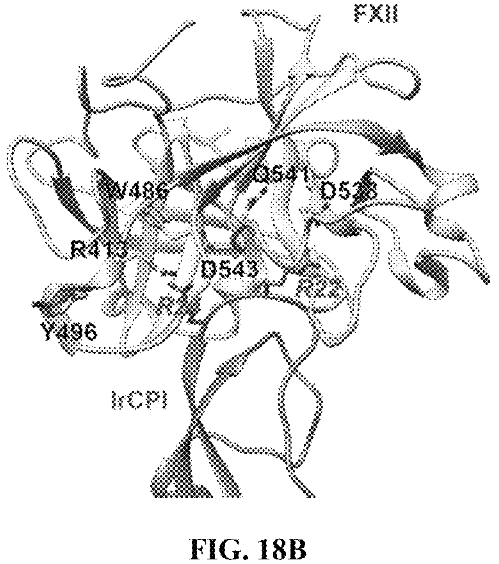

In the activated form, residues of the active site of FXIIa are correctly oriented and the substrate-binding pockets S−1 and S+1 in the catalytic domain of FXIIa are correctly formed (FIG. 18B), allowing the proper contact with residues R24 and R22 of Ir-CPI.

In silico analysis of FXII and FXIIa tridimensional structures indicates that it is highly unlikely that Ir-CPI interacts with FXII, while it shows that Ir-CPI would interact with FXIIa through its R22 and R24 residues.

Example 7: Assessment of the Effect of Ir-CPI on the Phagocytic Activity of Human Neutrophils

Materials and Methods

The effect of Ir-CPI on the phagocytic activity of human neutrophils was assessed. For this purpose, freshly isolated neutrophils from 3 donors were pre-treated for 1 h with recombinant Ir-CPI at 2 different concentrations (5.0 or 15.3 μg/mL) and then incubated in the presence of pH-rodo® *E. coli* bioparticles (Sartorius). To evaluate the phagocytic activity, fluorescence was monitored every 15 min for up to 48 hours.

Purification of Human Polymorphonuclear Neutrophils

Neutrophils were directly isolated from whole blood by using the EasySep™ Direct Human Neutrophil Isolation Kit (StemCell) and according to the manufacturer's protocol. The purification is a negative selection (elimination of unwanted cell populations) to obtain intact neutrophils.

Neutrophils Quality Control

Isolated cells were washed and labelled with a viability dye (Zombie Aqua™ Fixable Viability Kit; Biolegend). After 30 minutes of incubation, cells were washed and incubated with a mix of antibodies against neutrophils markers (anti-CD11b and anti-CD66b). After 30 minutes of incubation at 4° C., cells were washed and resuspended in DPBS-BSA 0.1% buffer before acquisition on the flow cytometer.

Phagocytosis Assay pHrodo® Green *E. coli* Bioparticles were resuspended at 1 mg/mL in PBS, vortexed and sonicated according to the manufacturer's protocol and then stored at 4° C. overnight. Then, 25.000 freshly isolated neutrophils, resuspended in RPMI 1640 medium containing 10% of FBS and supplements (2 mM Glutamine, 1% NEAA, 1 mM Sodium pyruvate, 50 μM β-mercaptoethanol and 50 μg/ml Gentamycin), were seeded per well in a 96 well-plate and preincubated for 1 h at 37° C., 5% CO2 with Ir-CPI at two different concentrations (2 μM and 0.65 μM). Then, pHrodo® Green *E. coli* Bioparticles were added at 10 μg/well and the plate was incubated in the Incucyte® Live-Cell Analysis System. Pictures were taken every 15 minutes for 48 hours. Two negative controls were performed: (1) only the neutrophils were seeded in absence of Ir-CPI and without particles, and (2) neutrophils were seeded in absence of Ir-CPI and incubated with the particles. All conditions were performed in triplicates.

Incucyte Read-Out

To analyse neutrophil phagocytosis, the Green total area (μm2/image) was measured in each well every 15 minutes for 48 hours (2 pictures/well). Briefly, the IncuCyte® Basic Analysis software allows for the quantification of fluorescent object metrics in real-time. The Basic analyzer enables to tailor phase segmentation parameters to individual cell types and experimental conditions, to accurately distinguish between background and positive fluorescent objects across a wide range of intensities.

Statistical Analysis

Statistical analysis was performed with JMP Pro version 15.

Results

Figure 19:
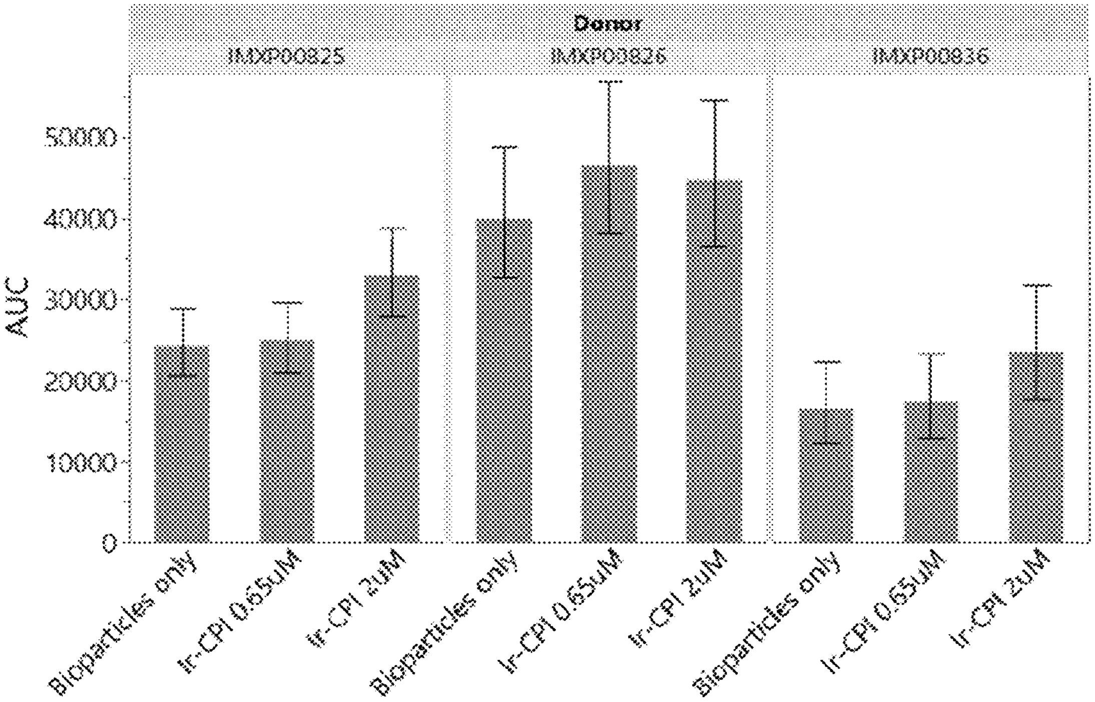
FIG. 19 is a set of histograms showing area under the curve (mean AUC) reflecting phagocytic activity, for each donor, until peak, back transformed to the original scale. Error bars represent 95% confidence intervals.

Overall, there was no evidence for an effect of Ir-CPI on neutrophil phagocytic activity at 5.0 μg/mL (0.65 μM). There was a marginal (p-value just below threshold for significance) evidence for an increase in the phagocytic activity with Ir-CPI at 15.3 μg/mL (2 μM) (FIG. 19). Ir-CPI, whatever the concentration, did not induce a decrease of the phagocytic activity of human neutrophils.

Example 8: Assessment of the Effect of Ir-CPI on Apoptosis Using Human Neutrophils

Materials and Methods

The effect of recombinant Ir-CPI on apoptosis/necrosis of human neutrophils was assessed. For this purpose, freshly isolated neutrophils from 4 donors were pre-treated for 1 h with recombinant Ir-CPI at 15.3 μg/mL and then incubated with Annexin V-FITC, with Propidium Iodide (PI) and with anti-human CD66b-PE antibody for cell identification. As negative control, neutrophils were only incubated with Annexin V-PI and CD66b for cell identification.

Purification of Human Polymorphonuclear Neutrophils

Polymorphonuclear neutrophils (PMNs) were isolated with StraightFrom® Whole Blood CD15 MicroBeads kits from Miltenyi Biotech. Briefly, after erythrocytes lysis, the blood cells were incubated in the presence of CD15 microbeads. Blood cells were washed with separation buffer and centrifuged at 300 g for 10 min at room temperature. The pellets containing magnetically labeled cells were resuspended in separation buffer and applied to the equilibrated whole blood column placed on the QuadroMACS. After extensive washing, the column was removed from the magnetic separator, and labeled cells were eluted using whole blood elution buffer. Finally, the PMNs were centrifuged at 300 g for 10 min and resuspended in Hank's buffer with calcium and magnesium. The neutrophil purity and activation state were verified by flow cytometry based on CD45/CD11b expression.

In Vitro Experiment

Apoptosis was detected by initially staining the cells with Annexin V and Propidium Iodide solution followed by flow cytometry analysis. Briefly, after isolation, neutrophils were incubated for 1 hour at 37° C. with or without Ir-CPI (2 μM for 400 000 PMNs in Hanks medium). Then, cells were incubated for 20 min at 4° C. with Annexin V-FITC (1/100), Propidium Iodide (PI) (1/100) (Tau Technology) and also with anti-human CD66b-PE antibody (1/100) (clone REA306, Miltenyi Biotech). Cells that were PI-negative and Annexin V-negative are considered healthy, PI-negative and Annexin V-positive cells are considered apoptotic, cells positive to both PI and Annexin V are considered dead, PI-positive and Annexin V-negative cells are considered necrotic.

Statistical Analysis

Analyses were performed using the GraphPad Prism software version 8.2.0.

Results

Figure 20:
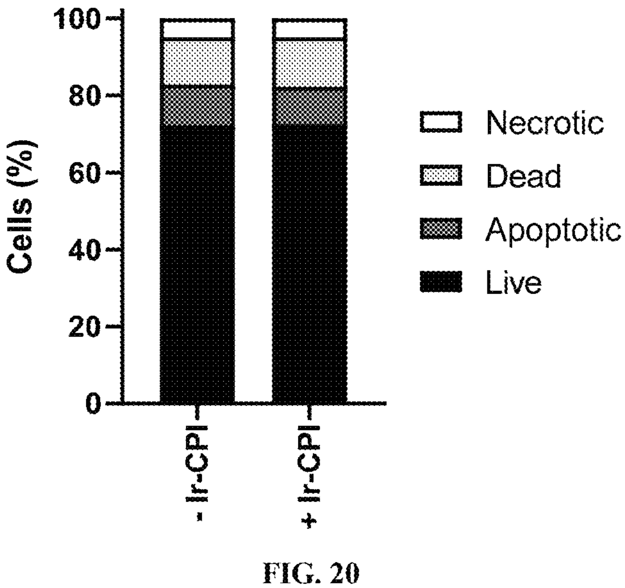
FIG. 20 is a set of histograms showing the effect of Ir-CPI on neutrophil apoptosis. Mean percentage of neutrophils are represented (n=4).

Ir-CPI did not induce apoptosis in human neutrophils following a 1 h incubation with these cells. There was no statistical difference in mean necrotic, dead, apoptotic, and live cells between the negative control condition and the condition using Ir-CPI (FIG. 20).

The unexpectedly superior result can be attributed to the ability of Ir-CPI to finely balance neutrophil functions, inhibiting their recruitment during thrombosis, without hindering their essential immune-related functions. This delicate equilibrium ensures effective immune responses while mitigating the risk of excessive inflammation and clot-related complications.

REFERENCES

Darbousset, R., et al. (2014). "P2X1 expressed on polymorphonuclear neutrophils and platelets is required for thrombosis in mice." Blood. 124(16):2575-2585.

Darbousset, R., et al. (2012). "Tissue factor-positive neutrophils bind to injured endothelial wall and initiate thrombus formation." Blood. 120(10):2133-2143.

Decrem, Y., et al. (2009). "Ir-CPI, a coagulation contact phase inhibitor from the tick *Ixodes ricinus*, inhibits thrombus formation without impairing hemostasis." J Exp Med. 206(11):2381-2395.

Demers, M., et al. (2012). "Cancers predispose neutrophils to release extracellular DNA traps that contribute to cancer-associated thrombosis." Proc Natl Acad Sci U.S.A. 109(32):13076-13081.

Dubois, C., et al. (2007). "Thrombin-initiated platelet activation in vivo is vWF independent during thrombus formation in a laser injury model." J Clin Invest; 117(4):953-960.

Dubois, C., et al. (2006). "Glycoprotein VI-dependent and-independent pathways of thrombus formation in vivo." Blood. 107(10):3902-3906.

Falati, S., et al. (2002). "Real-time in vivo imaging of platelets, tissue factor and fibrin during arterial thrombus formation in the mouse." Nat Med. 8(10):1175-1181.

Futosi, K., et al. (2013). "Neutrophil cell surface receptors and their intracellular signal transduction pathways." Int Immunopharmacol. 17(3):638-650.

Hu, Y. (2012). "Isolation of human and mouse neutrophils ex vivo and in vitro." Methods Mol Biol. 844:101-113.

Kambas, K., et al. (2012). "The emerging role of neutrophils in thrombosis-the journey of TF through NETs." Front Immunol. 3:385.

Keularts, I. M., et al. (2001). "The role of factor XI in thrombin generation induced by low concentrations of tissue factor." Thromb Haemost. 85(6):1060-1065.

Leal, A. C., et al. (2017). "Tumor-Derived Exosomes Induce the Formation of Neutrophil Extracellular Traps: Implications For The Establishment of Cancer-Associated Thrombosis." Sci Rep. 7(1):6438.

Massberg, S., et al. (2010). "Reciprocal coupling of coagulation and innate immunity via neutrophil serine proteases." Nat Med. 16(8):887-896.

Mauracher, L. M., et al. (2018). "Citrullinated histone H3, a biomarker of neutrophil extracellular trap formation, predicts the risk of venous thromboembolism in cancer patients." J Thromb Haemost.

Mezouar, S., et al. (2015). "Inhibition of platelet activation prevents the P-selectin and integrin-dependent accumulation of cancer cell microparticles and reduces tumor growth and metastasis in vivo." Int J Cancer. 136(2):462-475.

Thomas, G. M., et al. (2009). "Cancer cell-derived microparticles bearing P-selectin glycoprotein ligand 1 accelerate thrombus formation in vivo." J Exp Med. 206(9):1913-1927.

von Brühl, M. L., et al. (2012). "Monocytes, neutrophils, and platelets cooperate to initiate and propagate venous thrombosis in mice in vivo." J Exp Med. 209(4):819-835.

The invention claimed is:

1. A method of treating and/or reducing the likelihood of occurrence of thromboinflammation in a subject in need thereof, comprising administering to said subject a therapeutically effective amount of a protein or polypeptide comprising a polypeptide having the amino acid sequence SEQ ID NO: 2.

2. The method according to claim 1, wherein said protein or polypeptide binds to activated coagulation factors comprising FXIIa, FXIa, and kallikrein.

3. The method according to claim 1, wherein said thromboinflammation is selected from the group comprising atherosclerosis, plaque rupture, devices-induced thromboinflammation, thrombosis induced by catheterism and/or stent positioning procedures, thrombosis induced by extracorporeal circulation, thrombus formation following cerebral injuries, coronary artery disease, acute myocardial infarction, cancer-associated thrombosis, metastasis-associated thrombosis, stroke-associated thrombosis, Behçet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis, inflammatory bowel diseases, heparin-induced thrombocytopenia, immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

4. The method according to claim 3, wherein said thromboinflammation is thrombus formation following cerebral injuries.

5. The method according to claim 3, wherein said thromboinflammation is stroke-associated thrombosis.

6. A method of treating and/or reducing the likelihood of occurrence of thromboinflammation in a subject in need thereof, comprising administering to said subject a therapeutically effective amount of a medicament comprising a protein or polypeptide comprising:

a polypeptide having the amino acid sequence SEQ ID NO: 2, and at least one pharmaceutically acceptable excipient.

7. The method according to claim 6, wherein said protein or polypeptide binds to activated factors comprising FXIIa, FXIa, and kallikrein.

8. The method according to claim 6, wherein said thromboinflammation is selected from the group comprising atherosclerosis, plaque rupture, devices-induced thromboinflammation, thrombosis induced by catheterism and/or stent positioning procedures, thrombosis induced by extracorporeal circulation, thrombus formation following cerebral injuries, coronary artery disease, acute myocardial infarction, cancer-associated thrombosis, metastasis-associated thrombosis, stroke-associated thrombosis, Behçet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis, inflammatory bowel diseases, heparin-induced thrombocytopenia, immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

9. The method according to claim 8, wherein said thromboinflammation is thrombus formation following cerebral injuries.

10. The method according to claim 8, wherein said thromboinflammation is stroke-associated thrombosis.

* * * * *

SEQUENCE LISTING

```
Sequence total quantity: 3
SEQ ID NO: 1            moltype = AA  length = 67
FEATURE                 Location/Qualifiers
REGION                  1..67
                        note = polypeptide
source                  1..67
                        mol_type = protein
```

-continued

```
                        organism = Ixodes ricinus
SEQUENCE: 1
ANHKGRGRPA KCKLPPDDGP CRARIPSYYF DRKTKTCKEF MYGGCEGNEN NFENITTCQE  60
ECRAKKV                                                            67

SEQ ID NO: 2            moltype = AA  length = 67
FEATURE                 Location/Qualifiers
REGION                  1..67
                        note = polypeptide
source                  1..67
                        mol_type = protein
                        organism = Ixodes ricinus
SEQUENCE: 2
ANHKGRGRPA KCKLPPDDGP CRARIPSYYF DRKTKTCKEF MYGGCEGNEN NFEQITTCQE  60
ECRAKKV                                                            67

SEQ ID NO: 3            moltype = DNA  length = 201
FEATURE                 Location/Qualifiers
source                  1..201
                        mol_type = other DNA
                        organism = Ixodes ricinus
SEQUENCE: 3
gccaaccaca aaggtagagg gcggcctgcg aagtgtaaac ttcctccgga cgacggacca  60
tgcagagcac gaattccgag ttactacttt gatagaaaaa ccaaaacgtg caaggagttt  120
atgtatggcg gatgcgaagg aaacgaaaac aattttgaaa acataactac gtgccaagag  180
gaatgcagag caaaaaaagt c                                            201
```